United States Patent
Goodstal et al.

(10) Patent No.: US 11,202,419 B2
(45) Date of Patent: Dec. 21, 2021

(54) SOYBEANS WITH REDUCED ANTINUTRITIONAL FACTOR CONTENT

(71) Applicant: Arcadia Biosciences, Inc., Davis, CA (US)

(72) Inventors: Floyd John Goodstal, Davis, CA (US); Daniel Facciotti, Davis, CA (US)

(73) Assignee: ARCADIA BIOSCIENCES, INC., Phoenix, AZ (US)

( * ) Notice: Subject to any disclaimer, the term of this patent is extended or adjusted under 35 U.S.C. 154(b) by 0 days.

(21) Appl. No.: 16/816,751

(22) Filed: Mar. 12, 2020

(65) Prior Publication Data

US 2020/0291415 A1 Sep. 17, 2020

Related U.S. Application Data

(60) Provisional application No. 62/819,013, filed on Mar. 15, 2019.

(51) Int. Cl.
| | | |
|---|---|---|
| *A01H 1/06* | (2006.01) | |
| *A01H 6/54* | (2018.01) | |
| *A01H 5/10* | (2018.01) | |
| *C12N 15/82* | (2006.01) | |

(52) U.S. Cl.
CPC ............ *A01H 1/06* (2013.01); *A01H 5/10* (2013.01); *A01H 6/542* (2018.05); *C12N 15/8218* (2013.01); *C12N 15/8251* (2013.01)

(58) Field of Classification Search
None
See application file for complete search history.

(56) References Cited

U.S. PATENT DOCUMENTS

| | | | |
|---|---|---|---|
| 2008/0199591 A1 | 8/2008 | Saghai Maroof et al. | |
| 2014/0325714 A1* | 10/2014 | Gillman | A01H 5/10 800/312 |

FOREIGN PATENT DOCUMENTS

WO 2020190631 A1 9/2020

OTHER PUBLICATIONS

Zhou et al. The plant cyclin-dependent kinase inhibitor ICK1 has distinct functional domains for in vivo kinase inhibition, protein instability and nuclear localization. Plant J. Aug. 2003;35(4):476-89. (Year: 2003).*

Ohad et al. A similar structure of the herbicide binding site in photosystem II of plants and cyanobacteria is demonstrated by site specific mutagenesis of the psbA gene. Photosyn. Res. Jan. 1990;23(1):73-9. (Year: 1990).*

Arcadia Biosciences Improved soybean feed for use in aquaculture. Project Information (online) US Department of Agriculture. Aug. 31, 2018 [retrieved on Jun. 12, 2020 from the Internet: https://reeis.usda.gov/web/crisprojectpages/1010892-improved-soybean-feed-for-use-in-aquacul ture.html>. (Year: 2018).*

Gillman et al. The Low Phytic Acid Phenotype in Soybean Line CX1834 Is Due to Mutations in Two Homologs of the Maize Low Phytic Acid Gene. The Plant Genome. Jul. 2009. vol. 2, No. 2, pp. 179-190. (Year: 2009).*

International Search Report and Written Opinion for corresponding Application No. PCT/US20/22320 (dated Aug. 11, 2020).

Xie et al., "A Reference-Grade Wild Soybean Genome," Nature Communications 10:216 (2019).

Kuan et al., "Generation and Characterization of Two Novel Low Phytate Mutations in Soybean (Glycine max L. Merr.)," Theor. Appl. Genet. 115:945-957 (2007).

NCBI, GenBack accession No. RZC21057.1 (Feb. 13, 2019).
NCBI, GenBack accession No. RZB48327.1 (Feb. 13, 2019).

* cited by examiner

*Primary Examiner* — Cynthia E Collins
(74) *Attorney, Agent, or Firm* — Troutman Pepper Hamilton Sanders LLP (Rochester)

(57) ABSTRACT

Soybean plants with one or more non-transgenic human-induced mutations of the phytate transport genes, LPA-3 and LPA-19, and the agglutinin gene, LEC1, are disclosed. Soybean plants and seeds having reduced levels of phytate and/or lectin as a result of such non-transgenic human-induced mutations are provided. Meal prepared from soybean seeds provided herein is useful, for example, as a source of food or feed for poultry, human, swine, or fish, wherein the food or feed has reduced levels of antinutrient factors, including phytate and lectin.

11 Claims, No Drawings

Specification includes a Sequence Listing.

US 11,202,419 B2

SOYBEANS WITH REDUCED ANTINUTRITIONAL FACTOR CONTENT

CROSS-REFERENCE TO RELATED APPLICATIONS

This application is a non-provisional application of and claims the benefit of U.S. Provisional Application No. 62/819,013, filed Mar. 15, 2019, which is incorporated herein by reference in its entirety.

STATEMENT REGARDING FEDERALLY SPONSORED RESEARCH

This invention was made with Government support under SBIR grant number 2016-33610-25672 awarded by the U.S. Department of Agriculture. The Government has certain rights in the invention.

SUBMISSION OF SEQUENCE LISTING

A sequence listing containing the file named "ARC-40797_ST25.txt" which is 44942 bytes in size (measured in MS-Windows) and was created on Feb. 27, 2020, is provided herewith, and is incorporated herein by reference in its entirety.

FIELD

Non-naturally occurring soybean (*Glycine max*) plants, plant parts, seeds, and products thereof having reduced antinutrient factors (ANF) are described herein. This disclosure further provides non-transgenic human-induced mutations of the phytate transport genes, LPA-3 and LPA-19, and the agglutinin gene, LEC1, of soybean, and soybean plants having one or more of these non-transgenic mutations in their genome. In particular, the disclosure further provides soybean plants and seeds having reduced levels of phytate and/or lectin as a result of non-transgenic human-induced mutations in one or more LPA-3, LPA-19 and LEC1 genes. Methods and compositions that utilize the non-naturally occurring soybean plants and seeds having reduced antinutrients are also provided.

BACKGROUND

Soybean meal has long been a critical input for animal feed in monogastric animals (such as chickens and pigs) as it provides an ideal protein profile to promote healthy, rapid animal growth at a competitive price. More recently, aquaculture has sought to take advantage of the protein and cost advantages of soybean meal as an affordable protein substitute for more expensive and less sustainable fish feeds. The use of soybean feeds for ruminants and fish remains limited, however, due to the presence of anti-nutritional factors (ANF) including lectins that damage the intestinal lining, and phytate that binds to and prevents the uptake of proteins and essential cations. The aquaculture industry requires feed sources that deliver cost-effective inputs to maintain or increase feed conversion ratios (FCRs). Fishmeal and fish oil provide a highly digestible protein profile; however, the supply of fishmeal and oil from fisheries is not sufficient for aquaculture production needs, and new sources of fish feed are needed. Soybean meal is an alternative source for aquaculture feed due to its widespread production, cost efficiency, and attractive protein profile, but is limited by the presence of anti-nutritional factors that negatively impact digestibility. By way of example, salmon feed currently utilizes soybean on average at levels of approximately 8% of the feed content. Further, soybean used in aquaculture is treated harshly with heat or other processes to reduce or lower the antinutritional content, steps that increase production costs and reduce protein levels. Thus, there is a need for new soybean varieties having reduced levels of antinutrients for use in feeds for monogastric animals and in aquaculture.

Soybean plants store phosphate in its seeds in the form of phytic acid or phytate (myo-inositol 1,2,3,4, 5, 6-hexakisphosphate or InsP6). Phytate binds to cations and proteins in a non-digestible complex, reducing nutritional value of feed for fish and monogastric animals that lack the phytases capable of degrading the complex. This results in low availability of calcium, iron, zinc, magnesium and potassium as well as phosphate even though the seeds may contain high levels of these nutrients. The indigestibility of phytate in monogastric animals also leads to its presence in surface water runoff and its subsequent bacterial degradation, making it a major contributor to secondary pollution, which causes eutrophication of water bodies and contamination of ground water. Phytate biosynthesis and storage has been investigated in various plants. Gillman et al. (*The Plant Genome* (2009) 2:179-190) reported that mutations in two soybean ATP-binding cassette (ABC) transporter transport genes caused a reduction in phytate, with mutations in both genes necessary for the observed phenotype.

Lectins are carbohydrate-binding proteins that can be found in most plants and animals and are known for their specificity and high binding affinity for glycoproteins, glycolipids, and polysaccharides. Some plant lectins have antinutritional properties, decreasing their value for use in animal feed. A soybean lectin, agglutinin (SBA), has antinutritional properties which decreases the value of soybeans for use in animal feed. SBA causes a decrease in growth rate and loss of body weight when ingested by fish, poultry and mammals. Soybean content of 50% or greater in fish meal causes a decline in growth rate and non-specific immunity, and an increase in intestinal growth of the fish (Burrels et al. (1999) *Veterinary Immunology and Immunopathology* 72:277-288). Soybeans can be treated with heat to inactivate SBA, but this does not completely inactivate the SBA and can still lead to issues for consumers. In order to completely deactivate soy agglutinin, soybeans must be treated with denaturing enzymes after a physical treatment, such as heat. This extensive processing is costly and time consuming and makes soybeans less desirable for animal feed.

SUMMARY

In one embodiment, the disclosure relates to one or more human-induced, non-transgenic mutations in one or more of the following soybean genes: LPA-3, LPA-19, LEC1, and various combinations thereof.

In one embodiment, the disclosure relates to one or more non-transgenic mutations in one or more of the following soybean genes: LPA-3, LPA-19, LEC1 and various combinations thereof.

In one embodiment, the disclosure relates to mutations in LPA-3 selected from W328*, Q612* of SEQ ID NO. 2, and a missense mutation within the DNA encoding region of an ATP binding site of LPA-3. In one embodiment, a missense mutation of LPA-3 is G1330D of SEQ ID NO. 2.

In one embodiment, mutations in LPA-19 are selected from Q438* of SEQ ID NO. 4 and a missense mutation within the DNA encoding region of an ATP binding site of LPA-19. In one embodiment, a missense mutation of LPA-19 is G682S of SEQ ID NO. 4.

In one embodiment, the disclosure relates to a non-transgenic mutation in LEC1, wherein said mutation is L228* of SEQ ID NO. 6.

In another embodiment the disclosure relates to soybean plants, plant parts, and seeds comprising one or more mutations in one or more of the following gens: LPA-3, LPA-19, LEC1 and methods of obtaining such plants and seeds through transgenic or non-transgenic modification of soybean plants.

In another embodiment, the disclosure relates to methods for production of soybean lines where the seeds of such lines have reduced antinutritional factors by crossing soybean lines provided herein into additional soybean varieties In another embodiment, the disclosure relates to soybean seeds and soybean meal wherein said seeds and meal have reduced levels of antinutritional factors, including phytate and lectin.

In another embodiment, the disclosure relates to food or feed products prepared from soybean plants, plant parts and soybean seeds or meal having reduced levels of antinutritional factors.

In another embodiment, the disclosure relates to aquaculture feeds prepared from soybean plants, plant parts and soybean seeds or meal having reduced levels of antinutritional factors.

Other embodiments disclose methods of making and using soybean food products having reduced levels of phytate and lectin.

BRIEF DESCRIPTION OF THE SEQUENCES

SEQ ID NO: 1 shows *Glycine max* LPA-3 mRNA, complete cds. (Soybean Knowledge Base Glyma.03g167800).

SEQ ID NO: 2 shows the sequence of the LPA-3 protein encoded by SEQ ID NO: 1. SEQ ID NO 3 shows *Glycine max* LPA-19 mRNA, complete cds. (Soybean Knowledge Base Glyma.19g169000).

SEQ ID NO: 4 shows the shows the sequence of the LPA-19 protein encoded by SEQ ID NO: 3.

SEQ ID NO: 5 shows *Glycine max* LEC1 mRNA, complete cds. (Soybean Knowledge Base Glyma.02g01590).

SEQ ID NO: 6 shows the sequence of the LEC1 protein encoded by SEQ ID NO: 5.

SEQ ID NOs: 7 through 16 show exemplary primers for use in identifying useful mutations in LPA-3, LPA-19, and LEC1 genes.

SEQ ID NO: 17 shows a representative ATP binding site (GXXXXGKS).

DETAILED DESCRIPTION

Definitions

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1.000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the term "LPA-3" and "LPA-19" refer to the soybean genes located on chromosome 3 and chromosome 19 and their encoded proteins which function as MRP-type ABC (ATP binding cassette) transporters or "phytate transporters" or homologs, orthologs, paralogs and variants thereof. The term "LPA-3 gene" refers to variants, orthologs, homologs, paralogs, and functional equivalents of SEQ ID NO: 1 that codes for proteins that are similar to SEQ ID NO: 2. The term "LPA-19 gene" refers to variants orthologs, homologs, paralogs, and functional equivalents of SEQ ID NO: 3 that code for proteins that are similar to SEQ ID NO: 4.

As used herein, "ATP binding site" refers to peptide motifs in LPA-3 and LPA-19. Each of LPA-3 and LPA-19 contain two ATP binding sites (GXXXXGKS; SEQ ID NO: 17) located at amino acids 682-689 of LPA-3 and LPA-19 and at amino acids 1327-1334 of LPA-3 and amino acids 1325-1332 of LPA-19.

As used herein, the term "LEC1 refers to the single copy soybean gene on chromosome 2 and its encoded soybean agglutinin protein (SBA), also referred to herein as lectin, or homologs, orthologs, paralogs and variants thereof. The term "LEC1 gene" refers to variants, orthologs, homologs, paralogs, and functional equivalents of SEQ ID NO: 5 that codes for proteins that are similar to SEQ ID NO: 6.

As used herein, a "nonsense mutation" is mutation in which a sense codon corresponding to one of the twenty amino acids specified by the genetic code is modified to a chain-terminating codon.

As used herein, a "missense mutation" is mutation in which one or more nucleotides in a sense codon corresponding to one of the twenty amino acids specified by the genetic code is modified such that it codes for a different amino acid.

As used herein, a splice site mutation is a genetic mutation that inserts, deletes or changes a number of nucleotides in the specific site at which splicing takes place during the processing of precursor messenger RNA into mature messenger RNA As used herein, the term "allele" is any of one or more alternative forms of a gene, all of which relate to one trait or characteristic. In a diploid cell or organism, the two alleles of a given gene occupy corresponding loci on a pair of homologous chromosomes. An allele can be "wild-type" indicating the parental sequence at a particular nucleotide position, or "mutant" indicating a different nucleotide than the parental sequence. The term "heterozygous" indicates one wild-type and one mutant allele at a particular nucleotide position, and the term "homozygous" indicates two of the same allele at a particular nucleotide position.

As used herein, the terms "reducing," "reduced," "inhibited," "eliminated" or the like are considered relative terms, i.e. in comparison with the wild-type or unaltered state. As used herein "reduced" in reference to levels of antinutrients in soybean includes soybeans where the antinutrients levels are reduced in comparison to wild type soybean as well as to the point of non-detection and can be considered "eliminated." The "level of phytate" or "level of lectin" refer to the amounts of phytate or lectin that can be measured by any means known in the art. Phytate can be measured, for example, by HPLC separation and quantification (Lehrfeld, J, Journal of Agricultural and Food Chemistry, 42:2726-2731 (1994)). Lectin can be measured, for example, using an enzyme-linked adsorbent assay (Wang et al, Food Chemistry, 113:1218-1225 (2009)). "Reduced," "eliminated," "truncated," or "non-functional fragment" as used herein in reference to the function of a protein indicates that the protein has reduced biological activity as compared to the full native protein.

As used herein, amino acid or nucleotide sequence "identity" and "similarity" are determined from an optimal global alignment between the two sequences being compared. An optimal global alignment is achieved using, for example, the Needleman-Wunsch algorithm (Needleman and Wunsch, J. Mol. Biol. 48:443-453 (1970)). Sequences may also be aligned using algorithms known in the art including but not limited to CLUSTAL V algorithm or the BLASTN or BLAST 2 sequence programs.

As used herein, "control soybean seeds" are seeds from a soybean line having a similar genetic background to the soybean line from which the seeds being compared, i.e. low phytate and/or low lectin containing seeds, are obtained. It is understood that the control line or control seeds will not include mutations in LPA-3, LPA-19 or LEC1 genes as described herein, or transgenes resulting in reduced expression of LPA-3, LPA-19 or LEC1, and thus will have wildtype levels of phytate and/or lectin. Control seeds can include, for example, non-mutagenized seeds of the line used in mutagenesis, or segregating lines used in crosses where the segregants do not contain mutations in the LPA or LEC1 genes, and thus have a wildtype phenotype with respect to the phytate and lectin levels.

"Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the Blosum62 substitution matrix (Henikoff and Henikoff, 1992, Proc Natl Acad. Sci. USA 89: 10915-10919).

By the statement "sequence A is n % similar to sequence B," it is meant that n % of the positions of an optimal global alignment between sequences A and B consists of identical residues or nucleotides and conservative substitutions. By the statement "sequence A is n % identical to sequence B," it is meant that n % of the positions of an optimal global alignment between sequences A and B consists of identical residues or nucleotides.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides," that due to mutagenesis are not 100% identical but nevertheless code for the same amino acid sequence.

Overview

In one embodiment, the disclosure relates to a series of independent human-induced non-transgenic mutations in one or more soybean genes. In one embodiment, the disclosure relates to a series of independent human-induced non-transgenic mutations in one or more of the following soybean genes: LPA-3. LPA-19, LEC1 and various combinations thereof.

In another embodiment, the disclosure relates to methods of creating and identifying similar and/or additional mutations in LPA-3, LPA-19 and LEC1 genes in soybean. In another embodiment, soybean plants having mutations in LPA-3 and LPA-19 are disclosed. In another embodiment, soybean plants having mutations in LEC1 are disclosed. In another embodiment, the disclosure relates to soybean plants having mutations in LPA-3 and LEC1. In another embodiment, the disclosure relates to soybean plants having mutations in LPA-19 and LEC1. In another embodiment, the disclosure relates to soybean plants having mutations in LPA-3, LPA-19 and LEC1.

In another embodiment, the disclosure describes soybean plants having seeds with decreased phytate as a result of mutations in LPA-3 and LPA-19. In another embodiment, the disclosure describes soybean plants having seeds with decreased lectin as a result of mutations in LEC1.

In another embodiment, the disclosure describes soybean plants having seeds with decreased phytate, as compared to levels of phytate in wild type soybean, and decreased lectin, as compared to levels of lectin in wild type soybean. These non-naturally occurring soybean plants and seeds having reduced phytate and lectin levels can be created using methods known to those of skill in the art, including inhibiting the expression or reducing the stability or function of LPA-3, LPA-19 and LEC1 proteins.

In yet another embodiment, the disclosure describes soybean seeds having reduced levels of phytate and/or lectin, as compared to levels of phytate and lectin in control wild-type seeds and uses of the low phytate and/or low lectin seeds to produce one or more soybean food products. In another embodiment, a soybean food product with reduced phytate and lectin is provided for consumption by monogastric animals, including, for example, fish Representative Embodiments The disclosure describes soybean plants having seeds with reduced levels of antinutrient factors. In preferred embodiments, the reduced level of antinutrient factors is due to non-transgenic mutations and not the inclusion of foreign nucleic acids in the soybean plants' genomes. It should be understood that plants having these non-transgenic mutations may be bred with other transgenic plants having desired characteristics, i.e., herbicide, insect or pathogen resistance, or can be transformed with transgenes in order obtain other non-naturally occurring soybean plants with desired characteristics.

The described soybean plants and seeds can have phytate and/or lectin levels that are reduced by any amount as compared to wild type soybean plants and seeds that do not contain genetic alterations resulting in reduced LPA and/or LEC1 genes described herein. Soybean seeds can have a phytate content that is reduced by about 20% to 98% compared to levels in control soybean seeds or wild type seeds. For example, soybean seeds can have a phytate content that is reduced by about 98%, about 95%, about 90%, about 85%, about 80%, about 75%, about 70%, about 65%, about 60%/a, about 55%, about 50%, about 45%, about 40%, about 35%, about 30%, 25%, or about 20% compared to the levels of phytate in control wild type soybean seeds. In preferred embodiments, the seed phytate levels are reduced by at least 50% compared to the levels of phytate in control seeds or wild type seeds. Soybean seeds can have a lectin content that is reduced by about 20% to greater than 99% compared to levels in control soybean seeds or wild type seeds. In some embodiments, soybean seeds can have a lectin content that is undetectable by standard detection methods, or can have reduced levels of the protein such that lectin is detectable, but reduced by about 99%, about 98%, about 97%, about 96%, about 95%, about 94%, about 93%, about 92%, about 91%, about 90%, about 85%, about 80%, about 75%, about 70%/a, about 65%, about 60%, about 55%, about 50%, about 45%, about 40%, about 35%, about 30%/a, 25%, or about 20% compared to the levels of lectin in control soybean seeds or wild type seeds. In preferred embodiments, the seed lectin levels are reduced by at least 80% compared to the levels of lectin in control seeds or wild type seeds.

Representative LPA-3 and LPA-19 Mutations

In one embodiment, the disclosure relates to one or more human induced genetic alterations in the LPA-3 and/or LPA-19 genes. In one embodiment, the disclosure relates to one or more non-transgenic, human induced mutations in the LPA-3 and LPA-19 genes. The LPA-3 and LPA-19 genes may contain one or more non-transgenic mutations disclosed in Table 1. As LPA-3 and LPA-19 are homologous genes, the disclosure also encompasses corresponding mutations in each LPA allele, for example, mutations shown for LPA-3 are considered to encompass mutations in the corresponding regions in LPA-19, and mutations in LPA-19 are considered to encompass mutations in the corresponding regions in LPA-3. Corresponding mutations may not be in the exact location in each of the alleles, but one skilled in the art can identify the mutations using alignment technology.

In order to maximize the desired reduction in phytate levels in soybean seeds, mutations that reduce or eliminate the function of both LPA-3 and LPA-19 are desired, but soybeans and soybean seeds with one or more mutations in one gene are contemplated herein. In one embodiment, one or more mutations in LPA-3 and LPA-19 are nonsense mutations that result in truncated LPA proteins, where the truncated proteins have reduced activity, or the truncated proteins are non-functional fragments of the LPA protein. In one embodiment, nonsense mutations are located in DNA encoding from the N-terminus to the first ATP binding site in said LPA-3 or LPA-19 protein. In one embodiment, nonsense mutations are located in DNA encoding an ATP binding site in said LPA-3 or LPA-19 protein.

In one embodiment, one or more nonsense mutations are located in a DNA encoding region between the first ATP binding site in said LPA-3 or LPA-19 protein and the second ATP binding site in said LPA-3 or LPA-19 protein. In one embodiment, one or more mutations that reduce or eliminate the function of LPA-3 and/or LPA-19 are missense mutations. In one embodiment, a missense mutation that reduces or eliminates the function of LPA-3 and/or LPA-19 is located within a DNA encoding region for an LPA-3 or LPA-19 ATP binding site. In one embodiment, a missense mutation that reduces or eliminates the function of LPA-3 and/or LPA-19 is located in other parts of the LPA-3 or LPA-19 encoding region. Other mutations are also considered that reduce or eliminate the function of an LPA-3 or LPA-19 protein, including, for example mutations in the splice sites or promoter regions of the LPA-3 or LPA-19 genes.

Exemplary nonsense mutations in LPA-3 and LPA-19 include LPA-3 W328* of SEQ ID NO. 2, LPA-3 Q612* of SEQ ID NO. 2 and LPA-19 Q438* of SEQ ID NO. 4. Exemplary missense mutations in LPA-3 and LPA-19 include LPA-3 G1330D of SEQ ID NO. 2 and LPA-19 G682S of SEQ ID NO. 4, which are mutations in ATP binding sites.

These and other examples of mutations in LPA-3 and LPA-19 of soybean are provided in representative Tables 1 and 2 below. Nucleotide and amino acid changes are identified according to their positions in nucleotide and amino acid sequences. The Genotype column refers to whether the mutation is heterozygous or homozygous in the M2 plant. Nonsense mutations are indicated by an asterisk. Missense mutations are indicated noting the one letter code for the original amino acid, the position of the mutated amino acid in the protein sequence, and the one letter code for the amino acid in the mutated protein.

TABLE 1

Representative Mutations in LPA-3

| Primer SEQ IDs | LPA-3 Nucleotide Change (SEQ ID NO: 1) | LPA-3 Amino Acid Change (SEQ ID NO: 2) | Genotype |
| --- | --- | --- | --- |
| 7, 8 | G1124A | W328* | Heterozygote |
| 7, 8 | G1435A | W445* | Heterozygote |
| 7, 8 | G1453A | W451* | Heterozygote |
| 9, 10 | C1331T | R411* | Heterozygote |
| 9, 10 | G1453A | W451* | Heterozygote |
| 11, 12 | A5599T | K1303* | Heterozygote |
| 7, 8 | G1453A | W451* | Homozygote |
| 9, 10 | C2579T | Q788* | Homozygote |
| 9, 10 | T1986A | L629* | Homozygote |
| 9, 10 | C2543T | Q776* | Homozygote |
| 9, 10 | C1934T | Q612* | Homozygote |
| 9, 10 | A2331T | Splice Junction | Homozygote |
| 7, 8 | C1460T | P454S | Heterozygote |
| 9, 10 | G1711A | M537I | Heterozygote |
| 9, 10 | G2190T | G697V | Heterozygote |
| 9, 10 | C1460T | P454S | Heterozygote |
| 9, 10 | A1467T | Q456L | Heterozygote |
| 11, 12 | G5680A | G1330S | Heterozygote |
| 11, 12 | G5681A | G1330D | Heterozygote |
| 7, 8 | G542A | G134D | Heterozygote |
| 7, 8 | C280T | S52L | Homozygote |
| 9, 10 | G2496A | G760D | Homozygote |
| 9, 10 | G1713A | R538H | Homozygote |
| 9, 10 | G2585A | A790T | Homozygote |
| 9, 10 | C1457T | L453F | Homozygote |
| 9, 10 | G2496A | G760D | Homozygote |

TABLE 1-continued

Representative Mutations in LPA-3

| Primer SEQ IDs | LPA-3 Nucleotide Change (SEQ ID NO: 1) | LPA-3 Amino Acid Change (SEQ ID NO: 2) | Genotype |
|---|---|---|---|
| 9, 10 | A1467T | Q456L | Homozygote |
| 11, 12 | C5213T | R1243C | Homozygote |
| 11, 12 | G5214A | R1243H | Homozygote |
| 11, 12 | G5681A | G1330D | Homozygote |
| 11, 12 | G5680A | G1330S | Homozygote |
| 11, 12 | G5303A | E1273K | Homozygote |

TABLE 2

Representative Mutations in LPA-19

| Primer SEQ IDs | Nucleotide Change (SEQ ID NO: 3) | Amino Acid Mutation (SEQ ID NO: 4) | Genotype |
|---|---|---|---|
| 13, 14 | C1412T | Q438* | Heterozygote |
| 13, 14 | T1830A | L577* | Heterozygote |
| 13, 14 | A2330T | Splice Junction | Homozygote |
| 13, 14 | C2585T | A790V | Heterozygote |
| 13, 14 | G1679A | E527K | Homozygote |
| 13, 14 | G2144A | G682S | Heterozygote |
| 13, 14 | A1698T | K533I | Heterozygote |
| 13, 14 | C1481T | L461F | Heterozygote |
| 13, 14 | C1788T | P563L | Heterozygote |
| 13, 14 | G2552A | R779Q | Heterozygote |
| 13, 14 | C2566T | R784W | Heterozygote |

Representative LEC1 Mutations

The LEC1 gene exists as a single copy within the soybean genome. In one embodiment, the disclosure relates to one or more human-induced, non-transgenic mutations in the LEC1 gene. In some embodiments, the function of the LEC1 protein is reduced or eliminated by a nonsense mutation. In some embodiments, the function of the LEC1 protein is reduced or eliminated by one or more missense mutations.

An exemplary nonsense mutation in LEC1 is L228* of SEQ ID NO. 6. This and other examples of mutations in soybean LEC1 are provided in Table 3 below. Nucleotide and amino acid changes are identified according to their positions in nucleotide and amino acid sequences. The Genotype column refers to whether the mutation is heterozygous or homozygous in the M2 plant. Nonsense mutations are indicated by an asterisk. Missense mutations are indicated noting the one letter code for the original amino acid, the position of the mutated amino acid in the protein sequence, and the one letter code for the amino acid in the mutated protein. Other mutations are also considered which reduce or eliminate the function of the LEC1 protein, including, for example mutations in the splice sites or promoter regions of the LEC1 gene.

TABLE 3

Representative Mutations in LEC1

| Primer SEQ IDs | Nucleotide Change (SEQ ID NO: 5) | Amino Acid Mutation (SEQ ID NO: 6) | Genotype |
|---|---|---|---|
| 15, 16 | T1393A | L228* | Heterozygote |
| 15, 16 | T1393A | L228* | Homozygote |
| 15, 16 | G1202A | W164* | Heterozygote |
| 15, 16 | G1290A | A194T | Heterozygote |
| 15, 16 | G1434A | A242T | Heterozygote |
| 15, 16 | G1182A | D158N | Heterozygote |
| 15, 16 | G1203A | D165N | Heterozygote |
| 15, 16 | G987A | D93N | Heterozygote |
| 15, 16 | G1225A | G172E | Heterozygote |
| 15, 16 | G1443A | G245R | Heterozygote |
| 15, 16 | G999A | G97S | Heterozygote |
| 15, 16 | C948T | L80F | Heterozygote |
| 15, 16 | C1048T | P113L | Heterozygote |
| 15, 16 | C1216T | P169L | Heterozygote |
| 15, 16 | C933T | P75S | Heterozygote |
| 15, 16 | A1011T | S101C | Heterozygote |
| 15, 16 | C1378T | S223F | Heterozygote |
| 15, 16 | C1432T | S241F | Heterozygote |
| 15, 16 | C946T | S79F | Heterozygote |
| 15, 16 | C1261T | T184M | Heterozygote |
| 15, 16 | C1306T | T199I | Heterozygote |
| 15, 16 | C970T | T87I | Heterozygote |
| 15, 16 | G1233A | V175I | Heterozygote |
| 15, 16 | G1344A | V212I | Heterozygote |
| 15, 16 | G1005A | V99I | Heterozygote |
| 15, 16 | C1021T | A104V | Homozygote |
| 15, 16 | C1120T | A137V | Homozygote |
| 15, 16 | C1315T | A202V | Homozygote |
| 15, 16 | C808T | A33V | Homozygote |
| 15, 16 | G1203A | D165N | Homozygote |
| 15, 16 | G1444A | G245E | Homozygote |
| 15, 16 | C1476T | L256F | Homozygote |
| 15, 16 | C948T | L80F | Homozygote |
| 15, 16 | C933T | P75S | Homozygote |
| 15, 16 | C1024T | S105F | Homozygote |
| 15, 16 | C1378T | S223F | Homozygote |
| 15, 16 | C946T | S79F | Homozygote |
| 15, 16 | C1321T | T204I | Homozygote |
| 15, 16 | G1005A | V99I | Homozygote |

Identification of Representative Mutations

In one embodiment, mutations in soybean LPA-3, LPA-19, and LEC1 are created and identified using a method known as TILLING (Targeting Induced Local Lesions IN Genomes). See McCallum et al. Nature Biotechnology (2000) 18:455-457; McCallum et al. (2000) Plant Physiology 123:439-442; U.S. Publication No. 20040053236; and U.S. Pat. No. 5,994,075, all of which are incorporated herein by reference in their entirety. In the basic TILLING methodology, plant materials, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation can be grown into adult M3 plants and screened for the phenotypic characteristics associated with the gene of interest. In some cases, for example where mutations in multiple alleles are required, phenotypic effects are evaluated after breeding to combine mutant alleles into a single soybean plant line.

In one embodiment, seeds from soybean cultivar Jocketa are mutagenized and then grown into M1 plants. The M1 plants are allowed to self-pollinate and seeds from the M1 plant are grown into M2 plants, which are screened for mutations in their LPA-3, LPA-19 and LEC1 loci. One of skill in the art will understand that a variety of soybean plant materials, including, but not limited to, seeds, pollen, plant tissue or plant cells, may be mutagenized in order to create the mutated soybean plants disclosed herein, although the type of plant material mutagenized may affect when the plant DNA is screened for mutations.

Mutagens that create point mutations and deletions, insertions, transversions, and or transitions, such as chemical mutagens or radiation, may be used to create the mutations. Mutagens useful in the methods described herein include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7, 12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino] acridine dihydrochloride (ICR-170), formaldehyde, fast neutrons, and gamma irradiation. Spontaneous mutations in an LPA-3, LPA-19 or LEC1 gene that may not have been directly caused by the mutagen can also be identified.

Any suitable method of plant DNA preparation may be used to prepare the soybean DNA for mutation screening. For example, see Chen & Ronald, Plant Molecular Biology Reporter 17:53-57, 1999; Stewart and Via, Bio Techniques 14:748-749, 1993. Additionally, several commercial kits designed for this purpose are available, including kits from Qiagen (Valencia, Calif.) and Qbiogene (Carlsbad, Calif.).

In one embodiment, prepared DNA samples from individual soybean plants are pooled to expedite screening for mutations in one or more LPA-3, LPA-19 or LEC1 genes of the entire population of plants originating from the mutagenized plant tissue. The size of the pooled group may be varied depending on the sensitivity of the screening method used. Preferably, groups of two or more individual soybean plants are pooled.

In another embodiment, after DNA samples are pooled, the pools are subjected to sequence-specific amplification techniques, such as Polymerase Chain Reaction (PCR) using primers specific for LPA-3, LPA-19 or LEC1 genes. Any primer specific to an LPA-3, LPA-19 or LEC1 locus or the sequences immediately adjacent to one of these loci may be utilized to amplify the sequences within the pooled DNA sample. Preferably, the primer is designed to amplify the regions of the LPA-3, LPA-19 or LEC1 loci where useful mutations are most likely to arise. Most preferably, the primer is designed to detect exonic regions of one or more LPA-3, LPA-19 or LEC1 genes. Additionally, primers can be designed to target known polymorphic sites to facilitate screening for point mutations in a particular genome.

In one embodiment, primers are designed based upon the LPA-3, LPA-19 and LEC1 DNA sequences (SEQ ID NOs: 1, 3, and 5). Exemplary primers (SEQ ID NOs: 7-16) that have proven useful in identifying useful mutations within the LPA-3, LPA-19 and LEC1 sequences are provided in Example 1 herein.

In another embodiment, the PCR amplification products may be screened for LPA-3, LPA-19 and LEC1 mutations using any method that identifies nucleotide differences between wild type and mutant sequences. These may include, for example, without limitation, sequencing, denaturing high pressure liquid chromatography (dHPLC), constant denaturant capillary electrophoresis (CDCE), temperature gradient capillary electrophoresis (TGCE) (see Li et al, Electrophoresis 23(10): 1499-1511, 2002), or by fragmentation using enzymatic cleavage, such as used in the high throughput method described by Colbert et al. (*Plant Physiology* (2001) 126:480-484). Preferably, the PCR amplification products are incubated with an endonuclease that preferentially cleaves mismatches in heteroduplexes between wild type and mutant sequences. In another embodiment, cleavage products are electrophoresed using an automated sequencing gel apparatus, and gel images are analyzed with the aid of a standard commercial image-processing program.

In yet another embodiment, once an M2 plant having one or more mutations in an LPA-3, LPA-19 or LEC1 gene sequence is identified, the mutations are analyzed to determine their effect on the expression, translation, and/or activity of an LPA-3, LPA-19 or LEC1 protein. In one embodiment, the PCR fragment containing the mutation is sequenced, using standard sequencing techniques, in order to determine the exact location of the mutation in relation to the overall LPA-3, LPA-19 or LEC1 sequence. Each mutation is evaluated in order to predict its impact on protein function (i.e., from completely tolerated to causing loss-of-function) using bioinformatics tools such as SIFT (Sorting Intolerant from Tolerant; Ng and Henikoff, Nucleic Acids Research 31:3812-3814, 2003), PSSM (Position-Specific Scoring Matrix; Henikoff and Henikoff, Computer Applications in the Biosciences 12: 135-143, 1996) and PARSESNP (Taylor and Greene, Nucleic Acids Research 31:3808-3811, 2003). For example, a SIFT score that is less than 0.05 and a large change in PSSM score (e.g., roughly 10 or above) indicate a mutation that is likely to have a deleterious effect on protein function. These programs are known to be predictive, and it is understood by those skilled in the art that the predicted outcomes are not always accurate. In another embodiment, if the initial assessment of a mutation in the M2 plant indicates it to be of a useful nature and in a useful position within an LPA-3, LPA-19 or LEC1 gene, further phenotypic analysis of the soybean plant containing that mutation may be pursued. For mutations in an LPA protein, however, mutations in each of the LPA-3 and LPA-19 genes usually must be combined before a low phytate phenotype can be detected. The mutation containing plant can be backcrossed or outcrossed two times or more in order to eliminate background mutations at any generation. Then the backcrossed or outcrossed plant can be self-pollinated or crossed in order to create plants that are homozygous for the identified mutations.

Several physical characteristics of these homozygous LPA-3, LPA-19 and LEC1 mutant plants are assessed to determine if the mutations result in a useful phenotypic change in the soybean plant without resulting in undesirable negative effects, such as significantly reduced germination rates or seed yields.

Soybean Plants

In some embodiments, a soybean plant is produced that has one or more mutations in one or more of the following genes: LPA-3, LPA-19, LEC1 and various combinations thereof. In one embodiment, a soybean plant has one or more non-transgenic mutations identified in Tables 1-3. In one embodiment, a polynucleotide encoding a mutated LPA-3 or LPA-19 is about 85%, 86%, 87%, 88%, 89%, 90%, 91%, 92%, 93%, 94%, 95%, 96%, 97%, 98%, 99%, or greater than 99% identical to SEQ ID NO: 1 or SEQ ID NO:3, respectively. In another embodiment, a polynucleotide encoding a mutated LEC1 is about 85%, 86%, 87%, 88%, 89%, 90%, 91%, 92%, 93%, 94%, 95%, 96%, 97%, 98%, 99%, or greater than 99% identical to SEQ ID NO: 5.

In other embodiments, a soybean plant comprises a polynucleotide encoding a mutated LPA-3 or LPA-19, wherein the encoded LPA mutant protein is 85%, 86%, 87%, 88%, 89%, 90%, 91%, 92%, 93%, 94%, 95%, 96%, 97%, 98%, 99%, or greater than 99% identical to SEQ ID NO: 2 or SEQ ID NO:4, respectively. In yet another embodiment, a soybean plant comprises a polynucleotide encoding a mutated LEC1 protein, wherein the lectin mutant protein is 85%, 86%, 87%, 88%, 89%, 90%, 91%, 92%, 93%, 94%, 95%, 96%, 97%, 98%, 99%, or greater than 99% identical to SEQ ID NO: 6.

In some embodiments, soybean plants are produced using genetic engineering methods to modify the expression of one or more of the following genes: LPA-3, LPA-19, LEC1 and various combinations thereof. In some embodiments, transgenes that encode a polynucleotide that down-regulates the expression of LPA-3, LPA-19 or LEC1 genes or the activity of the LPA-3, LPA-19 or LEC1 proteins are employed. Examples of such polynucleotides include, but are not limited to, antisense polynucleotide, a sense polynucleotide, a catalytic polynucleotide, an artificial microRNA or a duplex RNA molecule. In some embodiments, genome editing, a specialized type of genetic engineering, is used to generate soybean plants having reduced expression or activity of an LPA-3, LPA-19, LEC1 protein and various combinations thereof.

In some embodiments, antisense molecules may include sequences that correspond to the structural gene or sequences that effect control over the gene expression or splicing event. For example, the antisense sequence may correspond to the coding region of LPA-3, LPA-19 or LEC1 or the 5'-untranslated region (UTR) or the 3'-UTR or any combination of these. It may be complementary in part to intron sequences, which may be spliced out during or after transcription, but preferably is complementary to exon sequences of the target gene. In view of the generally greater divergence of the UTRs, targeting these regions provides greater specificity of gene inhibition. The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences, which may function to stabilize the molecule.

Catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA). In some embodiments, the catalytic nucleic acid contains an antisense sequence for specific recognition of a target nucleic acid, and a nucleic acid cleaving enzymatic activity (also referred to as the "catalytic domain"). The ribozymes in plants disclosed herein and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase. As with antisense polynucleotides described herein, the catalytic polynucleotides should also be capable of hybridizing a target nucleic acid molecule (for example mRNA encoding LPA-3, LPA-19 or LEC1) under "physiological conditions", namely those conditions within a plant cell.

In some embodiments, RNA interference (RNAi) is useful for specifically inhibiting the production of one or more of LPA-3, LPA-19 or LEC1. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for use in the disclosed methods is described, for example in WO 99/32619, WO 99/53050, WO 99/49029, and WO 01/34815. In one embodiment, small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the barley plant in which it is to be introduced, e.g., as determined by standard BLAST search.

In one embodiment, microRNA regulation is used to down-regulate expression of one or more of LPA-3, LPA-19 or LEC1. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression.

In yet another embodiment, co-suppression regulation is used to down-regulate expression of one or more of LPA-3, LPA-19, LEC1 and various combinations thereof. The mechanism of co-suppression is thought to involve post-transcriptional gene silencing (PTGS) and in that regard may be similar to examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for antisense sequences described above. In some instances, the additional copy of the gene sequence interferes with the expression of the target plant gene. Reference is made to WO 97/20936 and EP 0465572 for methods of implementing co-suppression approaches.

In one embodiment, the disclosure relates to a plant with reduced expression of one or more of LPA-3, LPA-19 and LEC1 genes and/or reduced activity of one or more of LPA-3, LPA-19 and LEC1 proteins, wherein reduced gene expression and/or reduced protein activity is achieved by genomic editing. Genome editing, or genome editing with engineered nucleases (GEEN), is a type of genetic engineering in which DNA is inserted, replaced, or removed from a genome using artificially engineered nucleases, or "molecular scissors." The nucleases create specific double-stranded breaks (DSBs) at desired locations in the genome and harness the cell's endogenous mechanisms to repair the induced break by natural processes of homologous recombination (HR) and nonhomologous end-joining (NHEJ). There are currently four main families of engineered nucleases being used. Zinc finger nucleases (ZFNs), Transcription Activator-Like Effector Nucleases (TALENs), the CRISPR Cas system, and engineered meganuclease with re-engineered homing endonucleases.

In one embodiment, the disclosure relates to a plant with reduced expression of one or more of LPA-3, LPA-19 and LEC1 genes and/or reduced activity of one or more of LPA-3, LPA-19 and LEC1 proteins, wherein the reduced expression and/or activity results from the use of zinc-finger nucleases (ZFNs). ZFNs are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms. ZFNs consist of an engineered zinc finger DNA-binding domain fused to the cleavage domain of the FokI restriction endonuclease. ZFNs can be used to induce double-stranded breaks (DSBs) in specific DNA sequences and thereby promote site-specific homologous recombination with an exogenous template. The exogenous template contains the sequence that is to be introduced into the genome Publicly available methods for engineering zinc finger domains include Context-dependent Assembly (CoDA), Oligomerized Pool Engineering (OPEN), and Modular Assembly.

In one embodiment, the disclosure relates to reducing expression of one or more of LPA-3, LPA-19 and LEC1 genes and/or reduced activity of one or more of LPA-3, LPA-19 and LEC1 proteins using TALENs. TALEN is a sequence-specific endonuclease that consists of a transcription activator-like effector (TALE) and a FokI endonuclease. TALE is a DNA-binding protein that has a highly conserved central region with tandem repeat units of 34 amino acids. The base preference for each repeat unit is determined by two amino acid residues called the repeat-variable di-residue (RVD), which recognizes one specific nucleotide in the target DNA. Arrays of DNA-binding repeat units can be customized for targeting specific DNA sequences. As with ZFNs, dimerization of two TALENs on targeted specific sequences in a genome results in FokI-dependent introduction of DSBs, stimulating homology directed repair (HDR) and Non-homologous end joining (NHEJ) repair mechanisms.

In one embodiment, the disclosure relates to reducing expression of one or more of LPA-3, LPA-19 and LEC1 genes and/or reduced activity of one or more of LPA-3, LPA-19 and LEC1 proteins using the CRISPR/cas9 system. The Clustered Regularly Interspaced Short Palindromic Repeats (CRISPR.) Type II system is an RNA-Guided Endonuclease technology for genome engineering. There are two distinct components to this system, a guide RNA and an endonuclease, in this case the CRISPR associated (Cas) nuclease, Cas9. The guide RNA is a combination of the endogenous bacterial crRNA and tracrRNA into a single chimeric guide RNA (gRNA) transcript. The gRNA combines the targeting specificity of the crRNA with the scaffolding properties of the tracrRNA into a single transcript. When the gRNA and Cas9 are expressed in the cell, the genomic target sequence can be modified or permanently disrupted. The gRNA/Cas9 complex is recruited to the target sequence by the base-pairing between the gRNA sequence and the complementarity to the target sequence in the genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the wild-type Cas9 can cut both strands of DNA causing a Double Strand Break (DSB). Cas9 will cut 3-4 nucleotides upstream of the PAM sequence A DSB can be repaired through one of two general repair pathways: (1) NHEJ DNA repair pathway or (2) the HDR pathway. The NHEJ repair pathway often results in insertions/deletions (InDels) at the DSB site that can lead to frameshifts and/or premature stop codons, effectively disrupting the open reading frame (ORF) of the targeted gene. The HDR pathway requires the presence of a repair template, which is used to fix the DSB. HDR faithfully copies the sequence of the repair template to the cut target sequence. Specific nucleotide changes can be introduced into a targeted gene by the use of HDR with a repair template.

In one embodiment, the disclosure relates to reducing expression of one or more of LPA-3, LPA-19 and LEC1 genes and/or reducing activity of one or more of LPA-3, LPA-19 and LEC1 proteins using a meganuclease with a re-engineered homing nuclease. Meganucleases are endodeoxyribonucleases characterized by a large recognition site (double-stranded DNA sequences of 12 to 40 base pairs); as a result, this site generally occurs only once in any given genome. For example, the 18-base pair sequence recognized by the I-Sce1 meganuclease would on average require a genome twenty times the size of the human genome to be found once by chance (although sequences with a single mismatch occur about three times per human-sized genome). Meganucleases are therefore considered to be the most specific naturally occurring restriction enzymes. Among meganucleases, the LAGLIDADG family of homing endonucleases has become a valuable tool for the study of genomes and genome engineering over the past fifteen years. By modifying their recognition sequence through protein engineering, the targeted sequence can be changed Breeding with Soybean Plants In another embodiment, the disclosure is directed to methods for plant breeding using soybean plants and plant parts disclosed herein with one or more non-transgenic mutations in one or more of the following genes: the LPA-3, LPA-19, LEC1 and various combinations thereof.

One such embodiment is the method of crossing a soybean variety with one or more non-transgenic mutations in the LPA-3, LPA-19 or LEC1 genes with another variety of soybean to form a first generation population of F1 plants. One of ordinary skill in the art can utilize molecular methods to identify a particular F1 plant produced with one or more non-transgenic mutations in the LPA-3, LPA-19 or LEC1 genes, and any such individual plant is also encompassed by this invention. For example, conventional breeding techniques can be used with lines containing one or more non-transgenic mutations in the LPA-3, LPA-19 or LEC1 genes to produce lines having multiple traits, including both LPA-3 and LPA-19 mutant traits, or lines having mutations in all of the LPA-3, LPA-19 and LEC1 genes. These embodiments also cover use of backcross conversions of soybean varieties with one or more mutations in the LPA-3, LPA-19 or LEC1 genes to produce first generation F1 plants.

In another embodiment, the invention relates to a method of developing a progeny soybean plant. A method of developing a progeny soybean plant comprises crossing a soybean variety with one or more non-transgenic mutations in the LPA-3, LPA-19 or LEC1 genes with a second soybean plant and performing a breeding method. For example, one of ordinary skill in the art would cross a soybean variety with one or more non-transgenic mutations in the LPA-3, LPA-19 or LEC1 genes with another variety of soybean, such as an elite variety. The resulting F1 seed could be allowed to self or bred with another soybean cultivar. The process of growing and selection would be repeated any number of times until a homozygous soybean variety with one or more non-transgenic mutations in the LPA-3, LPA-19 or LEC1 genes is obtained.

Soybean Plants with Mutation Combinations

In some embodiments, plant lines homozygous for one or more identified mutations or, in other embodiments containing transgenes resulting in downregulation of LPA-3, LPA-19 or LEC1, are generated by standard breeding techniques to combine various mutations or transgenes. In some embodiments, down-regulation of combinations of LPA-3, LPA-19 and LEC1 are generated in a single plant using genetic engineering techniques, including the representative embodiments described above. In some embodiments, reducing expression of one or more of LPA-3, LPA-19 and LEC1 genes and/or reducing activity of one or more of LPA-3, LPA-19 and LEC1 proteins is accomplished by multiple approaches, with some gene modified by genetic engineering techniques and others by methods such as described herein.

In some embodiments using LPA-3 and LPA-19 mutants, homozygous lines for each allele are generated and used in further breeding to combine mutations in LPA-3 and LPA-19 in a single plant line. Double mutants are evaluated to determine the impact of the mutations on phytate seed composition. One skilled in the art will recognize that mutations in different genes or alleles can also be combined from lines that are heterologous for one or more of the mutations.

In one embodiment, double homozygous mutants for LPA-3 and LPA-19 comprise LPA-3 Q612* of SEQ ID NO. 2 and LPA-19 G682S of SEQ ID NO. 4. In one embodiment, double homozygous mutants comprise LPA-3 W328* of SEQ ID NO. 2 and LPA-19 G682S of SEQ ID NO. 4. In one embodiment, double homozygous mutants comprise LPA-3 W328* of SEQ ID NO. 2 and LPA-19 Q438* of SEQ ID NO. 4. In one embodiment, double homozygous mutants comprise LPA-3 G1330D of SEQ ID NO. 2 and LPA-19 Q438* of SEQ ID NO. 4. In one embodiment, double homozygous mutants comprise LPA-3 G1330D of SEQ ID NO. 2 and LPA-19 G682S of SEQ ID NO. 4. In some embodiments, double homozygous mutants comprise nonsense mutations in LPA-3 and LPA-19. In some embodiments, the nonsense mutations are located in DNA encoding from the N-terminus to the first ATP binding site. In some embodiments, double homozygous mutants comprise a nonsense mutation in one allele, LPA-3 or LPA-19, and a missense mutation in the other allele. In some embodiments, double LPA homozygous mutants comprise missense mutations in LPA-3 and LPA-19. In some embodiments, missense mutations are within the DNA encoding region of an ATP binding site (SEQ ID NO: 17) in LPA-3 or LPA-19. In some embodiments, missense mutations in the ATP binding site encoding region are mutations in the N-terminal ATP binding site. In some embodiments, missense mutations in the ATP binding site encoding region are mutations in the C-terminal ATP binding site.

LEC1 homozygous mutants are evaluated to determine seed lectin levels. In some embodiments, homozygous LEC1 mutants are obtained by standard breeding techniques from a soybean line heterologous for a LEC1 mutation. In some embodiments, homozygous mutants are identified in M2 lines resulting from mutagenesis, such as through TILLING as described herein.

Soybean plants with double homozygous LPA-3 and LPA-19 mutants identified as having desirable reductions in levels of phytate can be used in standard breeding techniques to generate additional soybean lines. In some embodiments, LPA-3/LPA-19 double mutants are crossed with soybean lines having reduced levels of seed lectin resulting from homozygous LEC1 mutations. In this manner, triple mutant soybean lines having reduced levels of phytate and reduced levels of lectin are obtained. In some embodiments, triple mutant soybean lines having mutations in LPA-3, LPA-19 and LEC1 comprise a nonsense mutation in LEC1. In some embodiments, triple mutant soybean lines having mutations in LPA-3, LPA-19 and LEC1 comprise a missense mutation in LEC1. In one embodiment, soybean mutant lines comprise LPA-3 Q612* of SEQ ID NO. 2, LPA-19 G682S of SEQ ID NO. 4, and LEC1 L228* of SEQ ID NO. 6. In one embodiment, soybean mutant lines comprise LPA-3 W328* of SEQ ID NO. 2, LPA-19 G682S of SEQ ID NO. 4, and LEC1 L228* of SEQ ID NO. 6. In one embodiment, soybean mutant lines comprise LPA-3 W328* of SEQ ID NO. 2, LPA-19 Q438* of SEQ ID NO. 4, and LEC1 L228* of SEQ ID NO. 6. In one embodiment, soybean mutant lines comprise LPA-3 G1330D of SEQ ID NO. 2, LPA-19 Q438* of SEQ ID NO. 4, and LEC1 L228* of SEQ ID NO. 6. In one embodiment, soybean mutant lines comprise LPA-3 G1330D of SEQ ID NO. 2, LPA-19 G682S of SEQ ID NO. 4, and LEC1 L228* of SEQ ID NO. 6. In some embodiments, triple mutant soybean lines comprise nonsense mutations in LPA-3, LPA-19 and LEC1. In some triple mutant soybean lines, the LPA-3 and LPA-19 nonsense mutations are located in DNA encoding from the N-terminus to the first ATP binding site. In some embodiments, soybean mutant lines comprise a nonsense mutation in LPA-3 or LPA-19, a missense mutation in the other LPA allele, and a missense or nonsense mutation in LEC1. In some embodiments, soybean mutant lines comprise missense mutations in LPA-3 and LPA-19, and a nonsense or missense mutation in LEC1. In some embodiments, triple mutant soybean lines comprise missense mutations within the DNA encoding region of an ATP binding site in LPA-3 or LPA-19, and a missense or nonsense mutation in LEC1. In some embodiments, missense mutations in the ATP binding site encoding region are mutations in the N-terminal ATP binding site. In some embodiments, missense mutations in the ATP binding site encoding region are mutations in the C-terminal ATP binding site.

Soybean Seeds

In some embodiments, soybean seeds from double homozygous LPA-3/LPA-19 mutants described herein, having reduced levels of phytate compared to controls seeds or wild type seeds are provided. It is understood that phytate levels in seeds from any particular mutant may vary depending on assay method, growing location, time of year and fertilization method. In some embodiments described herein, phytate reductions are determined by comparison of phytate levels in seeds from mutant soybean plants to seeds of genetically related plants grown at the same time and under the same conditions. In some embodiments, genetically related plants are wild type plants of the original mutated soybean mother line, Jocketa. In some embodiments, genetically related plants used as controls to compare levels of phytate are lines with wild type phytate content that segregate in crosses to generate homozygous soybean lines having mutations in LPA-3 and LPA-19.

Soybean seeds can have a phytate content that is reduced by about 20% to 98% compared to levels in control soybean seeds. In some embodiments, soybean seeds have a phytate content that is reduced by about 98%, about 95%, about 90%/a, about 85%, about 80%, about 75%, about 70%/a, about 65%, about 60%, about 55%, about 50%, about 45%, about 40%, about 35%, about 30%/a, 25%, or about 20% compared to the levels of phytate in control soybean seeds or wild type soybean seeds. In one embodiment, the seed phytate levels are reduced by at least 50% compared to the levels of phytate in control seeds or wild type seeds. In one embodiment, the seed phytate levels are reduced by at least 80% compared to the levels of phytate in control seeds or wild type seeds. In one embodiment, the seed phytate levels are reduced by at least 90% compared to the levels of phytate in control seeds or wild type seeds. In one embodiment, a soybean line comprises homozygous mutations LPA-3 Q612* of SEQ ID NO. 2 and LPA-19 G682S of SEQ ID NO. 4, and phytate is reduced by about 62% in comparison to phytate levels in control soybean seeds. In one embodiment, a soybean line comprises homozygous mutations LPA-3 W328* of SEQ ID NO. 2 and LPA-19 G682S of SEQ ID NO. 4, and phytate is reduced by about 52% in comparison to phytate levels in control soybean seeds. In one embodiment, a soybean line comprises homozygous mutations LPA-3 W328* of SEQ ID NO. 2 and LPA-19 Q438* of SEQ ID NO. 4 and phytate is reduced by about 88% in comparison to phytate levels in control soybean seeds. In one embodiment, a soybean line comprises homozygous mutations LPA-3 G1330D of SEQ ID NO. 2 and LPA-19 Q438* of SEQ ID NO. 4 and phytate is reduced by about 89% in comparison to phytate levels in control soybean seeds.

Soybean seeds can have a lectin content that is reduced by about 20% to greater than 99% compared to levels in control soybean seeds. Soybean seeds can have a lectin content that is undetectable by standard detection methods, or can have reduced levels of the protein such that lectin is detectable, but reduced by about 99%, about 98%, about 97%, about 96%, about 95%, about 94%, about 93%, about 92%, about 91%, about 90%/a, about 85%, about 80%, about 75%, about 70%/a, about 65%, about 60%, about 55%, about 50%, about 45%, about 40%, about 35%, about 30%/a, 25%, or about 20% compared to the levels of lectin in control soybean seeds or wild type soybean seeds. In one embodiment, seed lectin levels are reduced by at least 80% compared to the levels of lectin in control seeds. In one embodiment, seed lectin levels are reduced by at least 90% compared to the levels of lectin in control seeds or wild type seeds. In one embodiment, seed lectin levels are reduced by at least 95% compared to the levels of lectin in control seeds or wild type seeds. In one embodiment, lectin is reduced in mutants to levels that are undetectable by standard analytical means, such as an enzyme-linked lectin assay (ELLA) that uses carbohydrates to capture and detect lectin, or by hemagglutination technique using rabbit red blood cells. In one embodiment, a soybean line comprises a homozygous LEC1 L228* mutation of SEQ ID NO. 6, and lectin levels are reduced by greater than 90% compared to the levels of lectin in control seeds or wild type seeds. In one embodiment, a soybean line comprises a homozygous LEC1 L228* mutation of SEQ ID NO. 6 and lectin levels are undetectable by standard analytical methods.

In some embodiments, soybean seeds from plants having homozygous mutations in each of LPA-3, LPA-19 and LEC1 have reduced phytate and lectin levels. In some embodiments, soybean seeds having reduced phytate and lectin levels are from plants altered using genetic engineering methods as described above for reducing expression of one or more of LPA-3. LPA-19 and LEC1 genes and/or reducing activity of one or more of LPA-3, LPA-19 and LEC1 proteins. In some embodiments, soybean seeds having reduced levels of phytate and lectin are from plants generated using a combination of mutagenesis and genetic modification techniques. Soybean seeds can have a phytate content that is reduced by about 20% to 98% compared to levels in control soybean seeds or wild type soybean seeds and a lectin content that is reduced by about 20% to greater than 99% compared to levels in control soybean seeds or wild type soybean seeds. In some embodiments, the phytate content in soybean seeds is reduced by 98%, about 95%, about 90%, about 85%, about 80%, about 75%, about 70%, about 65%, about 60%, about 55%, about 50%, about 45%, about 40%, about 35%, about 30%, 25%, or about 20% compared to the levels of phytate in control soybean seeds or wild type soybean seeds, and the lectin is reduced by about 99%, about 98%, about 97%, about 96%, about 95%, about 94%, about 93%, about 92%, about 91%, about 90%, about 85%, about 80%, about 75%, about 70%, about 65%, about 60%, about 55%, about 50%, about 45%, about 40%, about 35%, about 30%, or about 25% compared to the levels of lectin in control soybean seeds or wild type soybean seeds. In some embodiments, soybean seeds from plants having homozygous mutations in each of LPA-3, LPA-19 and LEC1 have reduced phytate and lectin levels, where the phytate content is reduced by 98%, about 95%, about 90%, about 85%, about 80%, about 75%, about 70%, about 65%, about 60%, about 55%, about 50%, about 45%, about 40%, about 35%, about 30%, or about 25% compared to the levels of phytate in control soybean seeds or wild type soybean seeds, and the lectin is undetectable using standard analytic techniques. For example, in standard analytical procedures as described herein, lectin is not detectable at <0.375 mg/g. In one embodiment, soybean plants comprise homozygous mutations LPA-3 Q612* of SEQ ID NO. 2, LPA-19 G682S of SEQ ID NO. 4, and LEC1 L228* of SEQ ID NO. 6, and phytate is reduced in the seeds by about 70% in comparison to phytate levels in control soybean seeds or wild type soybean seeds, and lectin is reduced in the seeds by greater than 92% in comparison to control soybean seeds or wild type soybean seeds.

Soybean Food Products

Provided herein are soybean food and feed products, for use, for example in feed for monogastric animals, where the food and feed products have reduced levels of antinutritional factors in comparison to control soybean plants or wild-type soybean plants. In some embodiments, a representative antinutritional factor whose content is reduced in comparison to soybean feed products made from wildtype soybean is phytate. In some embodiments, an antinutritional factor whose content is reduced in comparison to soybean feed products made from wildtype soybean is lectin. In some embodiments, soybean feed products have reduced levels of phytate and lectin.

In some embodiments, a soybean feed product having reduced levels of phytate and/or lectin comprises full-fat soybean meal made from whole soybean seeds. In some embodiments, a soybean feed product having reduced levels of phytate and/or lectin comprises defatted soybean meal. In some embodiments a soybean feed product having reduced levels of phytate and/or lectin comprises ground soybean hulls. In some embodiments, a soybean feed product having reduced levels of phytate and/or lectin contains no hulls.

In some embodiments, soybean meal having reduced levels of antinutritional factors is used as animal feed for monogastric animals, including for example, pigs, poultry, horses, rabbits, and fish. In some embodiments, the soybean meal is defatted and used primarily as a protein supplement. In some embodiments, oil is present in the soybean meal. In some embodiments, all or a portion of the soybean seed oil is extracted during meal production. In other embodiments, oil from soybean or other vegetable sources is added to defatted soybean meal to provide additional sources of nutrition for animal consumption. In some embodiments, soybean food products having reduced levels of antinutritional factors find uses in products for human consumption, as humans are also monogastric and impacted by anti-nutritional factors in soybean. In some embodiments, soybean meal having reduced levels of phytate and/or lectin can also be used in feed for ruminants, although the advantages are greater when used in feed products for monogastric animals.

In some embodiments, reduced antinutrient soybean meal having reduced levels of phytate and/or lectin is used in aquaculture. In one embodiment, reduced antinutrient soybean meal having reduced levels of phytate and/or lectin can be used to replaces some, all, or a percentage of the fishmeal and fish oil that are the primary components of fish feed. In some embodiments, fish feed comprising reduced antinutrient soybean meal is used to feed salmonids, including without limitation pink salmon, chum salmon, coho salmon, masu salmon, sockeye salmon, Chinook salmon, Atlantic salmon, rainbow trout, sea trout, arctic char, brook trout, and lake trout. In some embodiments, fish feed comprising reduced antinutrient soybean meal is used to feed other fish species, including without limitation barramundi, bluegill and sunfish, catfish, golden shiner, hybrid striped bass, koi/carp, largemouth bass, sturgeon, tilapia, walleye, and yellow perch. Reduced antinutritional soybean meal provided herein will also find use in aquaculture for other species not named or for other species for which aquaculture methods are developed in the future.

In some embodiments, aquaculture feed prepared using soybean meal having reduced antinutritional factors as described herein, will comprise from approximately 25% to 75% protein depending on the type of fish being cultured. In general, the ratios of protein, oil and carbohydrate are determined for each fish species and one skilled in the art is capable of determining the amounts of protein, oil and carbohydrate that is appropriate for a particular species of interest. Salmon, by way of example, are generally supplied a diet with a protein content of 50% or higher. Thus, in some embodiments, defatted soybean meal having reduced antinutritional factors as described herein, will find use in salmon feed in view of the increased protein content of the meal obtained from defatted soybean seeds. In some embodiments, soybean seeds will also be dehulled to provide a soybean meal having reduced antinutritional factors and an even higher protein content. In some embodiments, soybean meal from defatted and dehulled soybean seeds is further processed to provide a soybean protein concentrate with crude protein levels of approximately 65%.

In some embodiments, aquaculture feed made from soybean meal having reduced antinutritional factors as described herein will be in the form of pellets, for example prepared by extrusion of ground ingredients. In some embodiments, additional ingredients in the soybean feed product having reduced antinutritional factors as described herein will include other components, including, but not limited to, fish meal, fish oil, vegetable proteins, vitamins, and binding agents.

In some embodiments, reduced antinutrient soybean meal will have reduced levels of lectin. In some embodiments, the reduced levels of lectin result from a homozygous nonsense mutation in the LEC1 gene. In some embodiments, the mutation is L228* of SEQ ID NO. 6. In some embodiments, the reduced levels of lectin result from one or more homozygous missense mutations in the LEC1 gene. Soybean meal can have a lectin content that is undetectable by standard detection methods, or can have reduced levels of the protein such that lectin is detectable, but reduced by about 99%, about 98%, about 97%, about 96%, about 95%, about 94%, about 93%, about 92%, about 91%, about 90%, about 85%, about 80%, about 75%, about 70%, about 65%, about 60%, about 55%, about 50%, about 45%, about 40%, about 35%, about 30%, 25%, or about 20% compared to the levels of lectin in meal prepared from control soybean seeds or wild type soybean seeds. In preferred embodiments, the soybean meal lectin levels are reduced by at least 80% or 90% compared to the levels of lectin in meal prepared from control seeds or wildtype seeds.

In some embodiments the antinutrient soybean meal with reduced lectin content will be present as a percentage of fish meal. In some embodiments, antinutrient soybean meal will be present as 1%, 2%, 3%, 4%, 5%, 6%, 7%, 8%, 9%, 10% to 20%, 20% to 30%, 30% to 40%, 40% to 50%, 50% to 60%, 60% to 70%, 70% to 80%, 80% to 90%, 90% to 99%, or up to 100% of the fish feed content.

In one embodiment, 50% of a fish meal diet is replaced with soybean meal prepared from a reduced or "no lectin" soybean mutant having a homozygous mutation L228* of SEQ ID NO. 6 resulting in improved weight gain versus a meal containing 50% soybean meal prepared from wild type soybeans or control soybeans.

In some embodiments, reduced antinutrient soybean meal will have reduced levels of phytate. In some embodiments, the reduced levels of phytate result from homozygous nonsense mutations in the LPA-3 and LPA-19 genes. In one embodiment, nonsense mutations are located in DNA encoding from the N-terminus to the first ATP binding site in said LPA-3 or LPA-19 protein. In one embodiment, nonsense mutations are located in DNA encoding an ATP binding site in said LPA-3 or LPA-19 protein. In one embodiment, nonsense mutations are located in a DNA encoding region between the first ATP binding site in said LPA-3 or LPA-19 protein and the second ATP binding site in said LPA-3 or LPA-19 protein. In one embodiment, mutations that reduce or eliminate the function of LPA-3 and/or LPA-19 resulting in reduced phytate levels are missense mutations. In one embodiment, a missense mutation is located within a DNA encoding region for an LPA-3 or LPA-19 ATP binding site. In one embodiment, a missense mutation that reduces or eliminates the function of LPA-3 and/or LPA-19 is located in other portions of the LPA-3 or LPA-19 encoding region. Other mutations are also considered which reduce or eliminate the function of an LPA-3 or LPA-19 protein and result in reduced levels of phytate in soybean seeds, including, for example mutations in the splice sites or promoter regions of the LPA-3 or LPA-19 genes.

Exemplary mutations that result in reduced phytate in soybean seeds include nonsense mutations in LPA-3 and LPA-19 disclosed herein, including LPA-3 W328* of SEQ ID NO. 2, LPA-3 Q612* of SEQ ID NO. 2 and LPA-19 Q438* of SEQ ID NO. 4. Exemplary missense mutations in LPA-3 and LPA-19 include LPA-3 G1330D of SEQ ID NO. 2 and LPA-19 G682S of SEQ ID NO. 4, which are mutations in ATP binding sites. In some embodiments, soybean meal having reduced phytate is prepared from soybean plants having homozygous mutations in LPA-3 and LPA-19 exemplified herein. In one embodiment, double homozygous mutants for LPA-3 and LPA-19 comprise LPA-3 Q612* of SEQ ID NO. 2 and LPA-19 G682S of SEQ ID NO. 4. In one embodiment, double homozygous mutants comprise LPA-3 W328* of SEQ ID NO. 2 and LPA-19 G682S of SEQ ID NO. 4. In one embodiment, double homozygous mutants comprise LPA-3 W328* of SEQ ID NO. 2 and LPA-19 Q438* of SEQ ID NO. 4. In one embodiment, double homozygous mutants comprise LPA-3 G1330D of SEQ ID NO. 2 and LPA-19 Q438* of SEQ ID NO. 4. In one embodiment, double homozygous mutants comprise LPA-3 G1330D of SEQ ID NO. 2 and LPA-19 G682S of SEQ ID NO. 4.

Soybean meal can have a phytate content that is reduced by about 20% to 98% compared to levels in control soybean seeds. In some embodiments phytate in soybean meal is reduced by about 98%, about 95%, about 90%, about 85%, about 80%, about 75%, about 70%, about 65%, about 60%, about 55%, about 50%, about 45%, about 40%, about 35%, about 30%, 25%, or about 20% compared to the levels of phytate in control soybean seeds or wild type soybean seeds. In preferred embodiments, the soybean meal phytate levels are reduced by at least 80% or 90% compared to the levels of lectin in meal prepared from wildtype seeds or control seeds.

In some embodiments the antinutrient soybean meal with reduced phytate content will be present at levels of from 1% up to 100% of a fish feed. In some embodiments, antinutrient soybean meal having low levels of phytate will be present at 1%, 2%, 3%, 4%, 5%, 6%, 7%, 8%, 9%, 10% to 20%, 20% to 30%, 30% to 40%, 40% to 50%, 50% to 60%, 60% to 70%, 70% to 80%, 80% to 90%, 90% to 99%, or up to 100% of the fish feed content. In some embodiments, reduced antinutrient soybean meal will have reduced levels of phytate and reduced levels of lectin as the result of mutants and methods described herein. In some embodiments the antinutrient soybean meal with reduced phytate and lectin content will be present at levels of from 1% up to 100% of a fish feed. In some embodiments, antinutrient soybean meal having reduced phytate and lectin will be present as 1%, 2%, 3%, 4%, 5%, 6%, 7%, 8%, 9%, 10% to 20%, 20% to 30%, 30% to 40%, 40% to 50%, 50% to 60%, 60% to 70%, 70% to 80%, 80% to 90%, 90% to 99%, or up to 100% of the fish feed content.

In some embodiments, soybean meal having reduced phytate and lectin is prepared from triple mutant soybean lines having mutations in LPA-3, LPA-19 and LEC1. In some embodiments, soybean lines used for preparation of low phytate and low lectin meal comprise double homozygous mutations in LPA-3 and LPA-19 as described above for soybean plants used to produce low phytate soybean meal, and a nonsense mutation in LEC1. In some embodiments, triple mutant soybean lines used for production of low phytate and low lectin soybean meal and having mutations in LPA-3, LPA-19 and LEC1 comprise a missense mutation in LEC1. In some embodiments, triple mutant soybean lines for production of low phytate and low lectin soybean meal comprise nonsense mutations in LPA-3, LPA-19 and LEC1. In some triple mutant soybean lines, the LPA-3 and LPA-19 nonsense mutations are located in DNA encoding from the N-terminus to the first ATP binding site. In some embodiments, soybean mutant lines for production of low phytate and low lectin soybean meal comprise a nonsense mutation in LPA-3 or LPA-19, a missense mutation in the other LPA allele, and a missense or nonsense mutation in LEC1. In some embodiments, soybean mutant lines for production of low phytate and low lectin soybean meal comprise missense mutations in LPA-3 and LPA-19, and a nonsense or missense mutation in LEC1. In some embodiments, triple mutant soybean lines for production of low phytate and low lectin soybean meal comprise missense mutations within the DNA encoding region of an ATP binding site in LPA-3 or LPA-19, and a missense or nonsense mutation in LEC1. In some embodiments, missense mutations in the ATP binding site encoding region are mutations in the N-terminal ATP binding site. In some embodiments, missense mutations in the ATP binding site encoding region are mutations in the C-terminal ATP binding site.

In one embodiment, soybean mutant lines for production of low phytate and low lectin soybean meal comprise LPA-3 Q612* of SEQ ID NO. 2, LPA-19 G682S of SEQ ID NO. 4, and LEC1 L228* of SEQ ID NO. 6. In one embodiment, soybean mutant lines for production of low phytate and low lectin soybean meal comprise LPA-3 W328* of SEQ ID NO. 2, LPA-19 G682S of SEQ ID NO. 4, and LEC1 L228* of SEQ ID NO. 6. In one embodiment, soybean mutant lines comprise LPA-3 W328* of SEQ ID NO. 2, LPA-19 Q438* of SEQ ID NO. 4, and LEC1 L228* of SEQ ID NO. 6. In one embodiment, soybean mutant lines for production of low phytate and low lectin soybean meal comprise LPA-3 G1330D of SEQ ID NO. 3, LPA-19 Q438* of SEQ ID NO. 4, and LEC1 L228* of SEQ ID NO. 6. In one embodiment, soybean mutant lines for production of low phytate and low lectin soybean meal comprise LPA-3 G1330D of SEQ ID NO. 2, LPA-19 G682S of SEQ ID NO. 4, and LEC1 L228* of SEQ ID NO. 6.

The plants, plant parts, seeds, and products thereof, and methods are further described by the following statements:

1. A soybean plant comprising one or more non-transgenic mutations in each of LPA-3 and LPA-19, wherein said mutation in LPA-3 is selected from the group consisting of: W328* of SEQ ID NO. 2, Q612* of SEQ ID NO. 2, and a missense mutation within the DNA encoding region of an ATP binding site of LPA-3, and said mutation in LPA-19 is selected from Q438* of SEQ ID NO. 4 and a missense mutation within the DNA encoding region of an ATP binding site of LPA-19.

2. A soybean plant of paragraph 1 wherein said missense mutation within the DNA encoding region of LPA-3 is G1330D of SEQ ID NO. 2.

3. A soybean plant of any of the preceding paragraphs wherein said missense mutation within the DNA encoding region of LPA-19 is G682S of SEQ ID NO. 4.

4. A soybean plant of any of the preceding paragraphs wherein said mutation in LPA-3 is Q612* of SEQ ID NO. 2 and said mutation in LPA-19 is G682S of SEQ ID NO 4.

5. A soybean plant of any of the preceding paragraphs wherein said mutation in LPA-3 is G1330D of SEQ ID NO. 2 and said mutation in LPA-19 is Q438* of SEQ ID NO. 4.

6. A soybean plant of any of the preceding paragraphs wherein said mutation in LPA-3 is W328* of SEQ ID NO. 2 and said mutation in LPA-19 is G682S of SEQ ID NO. 4.

7. A soybean plant of any of the preceding paragraphs wherein said mutation in LPA-3 is W328*of SEQ ID NO. 2 and said mutation in LPA-19 is Q438* of SEQ ID NO. 4.

8. A soybean plant of any of the preceding paragraphs wherein the phytate content of seeds of said plant is reduced by at least 50% compared to the phytate content of seeds of a non-mutagenized parent soybean plant.

9. A soybean plant of any of the preceding paragraphs wherein the phytate content of seeds of said plant is reduced by at least 80% compared to the phytate content of seeds of a non-mutagenized parent soybean plant.

10. Seed from a soybean plant of any of the preceding paragraphs.

11. Soybean meal prepared from a soybean seed of any of the preceding paragraphs.

12. A food product prepared using soybean meal of paragraph 11.

13. The food product of paragraph 12 wherein said product is for consumption by a monogastric animal.

14. The food product of paragraph 13 wherein said monogastric animal is poultry, human, swine, or fish.

15. A soybean plant comprising a homozygous mutation in LEC1, wherein said mutation is L228* of SEQ ID NO. 6, and wherein seeds of said soybean plant have reduced lectin levels as compared to lectin levels in seeds of a non-mutagenized soybean parent plant.

16. A soybean plant of any of the preceding paragraphs wherein seed yield of said plant is comparable to seed yield of a non-mutagenized parent line.

17. A soybean plant of any of the preceding paragraphs, wherein seeds of said soybean plant have undetectable levels of lectin by standard analysis.

18. A soybean plant of any of the preceding paragraphs, wherein the lectin content of seeds of said plant is reduced by at least 50% compared to the lectin content of seeds of a non-mutagenized parent soybean plant.

19. Seed from a soybean plant of any of the preceding paragraphs.

20. Soybean meal prepared from soybean seed of any of the preceding paragraphs.

21. A food product prepared from soybean meal of any of the preceding paragraphs.

22. The food product of paragraph 21 wherein said product is for consumption by a monogastric animal.

23. The food product of paragraph 22 wherein said monogastric animal is poultry, human, swine, or fish.

24. The food product of paragraph 23, wherein up to 50% of the food product is soybean meal.

25. A soybean plant comprising homozygous mutations in LPA-3, LPA-19 and LEC1, wherein the seeds of said soybean plant have reduced phytate and lectin as compared to phytate and lectin levels in seeds of a non-mutagenized soybean parent plant.

26. A soybean plant of claim 25 wherein said mutations in LPA-3 and LPA-19 are selected from (i) a nonsense mutation in said LPA-3 or LPA-19 protein, and (ii) a missense mutation within the DNA encoding region an ATP binding site of said LPA-3 or LPA-19 protein.

27. A soybean plant of claim 25 wherein said homozygous mutations in LPA-3 and LPA-19 are nonsense mutation.

28. A soybean plant of claim 25 wherein said phytate is reduced in said seeds by at least 50% and the lectin is reduced in said seeds by at least 90% compared to the phytate and lectin content of seeds of a non-mutagenized control soybean plant.

29. Soybean seed from a soybean plant of paragraph 25.

30. Soybean seed of any of the preceding paragraphs, wherein the phytate content is reduced by at least 50% compared to the phytate content of seeds of a non-mutagenized parent soybean plant.

31. Soybean seed of any of the preceding paragraphs, wherein the lectin content is reduced by at least 90% compared to the phytate content of seeds of a non-mutagenized parent soybean plant.

32. Soybean seed of any of the preceding paragraphs wherein lectin is undetectable in said seeds.

33. Soybean meal prepared from a soybean seed of any of the preceding paragraphs 2.

34. A food product prepared using soybean meal of paragraph 33.

35. The food product of paragraph 34 wherein said product is for consumption by a monogastric animal.

36. The food product of paragraph 35 wherein said monogastric animal is poultry, human, swine, or fish.

37. A food product for consumption by a monogastric animal, wherein said food product is prepared using soybean seeds or soybean meal prepared from said soybean seeds, wherein said soybean seeds have reduced phytate and lectin as the result of genetic modifications of LPA-3, LPA-19 and LEC1 in plants from which the seeds are harvested.

38. A food product of paragraph 37, wherein said genetic modifications are homozygous mutations in LPA-3, LPA-19 and LEC1.

39. A food product of paragraph 38, wherein said homozygous mutations in LPA-3 and LPA-19 are selected from (i) a nonsense mutation in said LPA-3 or LPA-19 protein, and (ii) a missense mutation within the DNA encoding region an ATP binding site of said LPA-3 or LPA-19 protein.

40. A food product of paragraph 39, wherein said homozygous mutations in LEC1 is a nonsense mutation.

41. A food product of paragraph 37 wherein said monogastric animal is poultry, human, swine, or fish.

42. A food product of paragraph 41 wherein said fish is a salmonid.

43. A food product of paragraph 41, wherein said soybean meal comprises greater than 2% of the contents of said food product.

44. A food product of paragraph 41, wherein said soybean meal comprises up to 50% of the contents of said food product.

45. A food product of paragraph 37 wherein lectin is undetectable.

46. A soybean plant comprising human-induced genetic modifications in LPA-3, LPA-19 and LEC1 that provide for reduced levels of phytate and lectin in seeds of said soybean plant as compared to phytate and lectin levels in seeds of a soybean control plant lacking the genetic modifications in LPA-3, LPA-19 and LEC1.

47. The soybean plant of paragraph 46 wherein said mutation in LPA-3 is Q612*, said mutation in LPA-19 is G682S and said mutation in LEC1 is L228*.

48. Soybean seed from a soybean plant of paragraphs 46 or 47.

49. Soybean meal prepared from soybean seeds of paragraph 48.

50. A food product prepared using soybean seeds of paragraph 48 or soybean meal of paragraph 49.

51. The food product of paragraph 50 wherein said product is for consumption by a monogastric animal.

52. The food product of paragraph 51 wherein said monogastric animal is poultry, human, swine, or fish.

53. A method for making a soybean food product that has reduced levels of phytate and/or lectin comprising processing seeds from a soybean plant of paragraphs 8, 18 or 25

54. The method of paragraph 53 wherein said food product is for consumption by a monogastric animal.

55. The method of paragraph 54 wherein said monogastric animal is poultry, human, swine, or fish.

56. Use of a food product of paragraph 51 for feeding a monogastric animal

REPRESENTATIVE EXAMPLES

Example 1: Representative Methods for Identification of Soybean Mutants

Mutagenesis

Soybean seeds were placed on a shaker (45 rpm) in a fume hood at ambient temperature. The mutagen ethyl methanesulfonate (EMS) was added to the imbibing seeds to final concentrations ranging from about 0.2% to about 1.6% (v/v). Following an incubation of 6 to 24 hours, the EMS solution was replaced 4 times with fresh H₂O. The seeds were then rinsed under running water for approximately 1 hour. Finally, the mutagenized seeds were planted (96/tray) in potting soil and allowed to germinate indoors. Plants that were four to six weeks old were transferred to the field to grow to fully mature M plants. The mature M1 plants were allowed to self-pollinate and then seeds from the M1 plant were collected and planted to produce M2 plants DNA Preparation DNA from M2 plants was extracted and prepared in order to identify the M2 plants that carried a mutation at their LPA3, LPA19 or LEC1 loci. The M2 plant DNA was prepared using the methods and reagents contained in the Qiagen® (Valencia, Calif.) DNeasy® 96 Plant Kit. Approximately 50 mg of frozen plant sample was placed in a sample tube with a tungsten bead, frozen in liquid nitrogen and ground 2 times for 1 minute each at 20 Hz using the Retsch® Mixer Mill MM 300. Next 400 µl of solution AP1 [Buffer AP1, solution DX and RNase (100 mg/ml)] at 80° C. was added to the sample. The tube was sealed and shaken for 15 seconds. Following the addition of 130 µl Buffer AP2, the tube was shaken for 15 seconds. The samples were placed in a freezer at minus 20° C. for at least 1 hour. The samples were then centrifuged for 20 minutes at 5600×g. A 400 µl aliquot of supernatant was transferred to another sample tube. Following the addition of 600 µl of Buffer AP3E, this sample tube was capped and shaken for 15 seconds. A filter plate was placed on a square well block and 1 ml of the sample solution was applied to each well and the plate was sealed. The plate and block were centrifuged for 4 minutes at 5600×g Next, 800 µl of Buffer AW was added to each well of the filter plate, sealed and spun for 15 minutes at 5600×g in the square well block. The filter plate was then placed on a new set of sample tubes and 80 µl of Buffer AE was applied to the filter. It was capped and incubated at room temperature for 1 minute and then spun for 2 minutes at 5600×g. This step was repeated with an additional 80 µl Buffer AE. The filter plate was removed and the tubes containing the pooled filtrates were capped. The individual samples were then normalized to a DNA concentration of 5 to 10 ng/µl.

Tilling

The M2 DNA was pooled into groups of six individual plants. The DNA concentration for each individual within the pool was approximately 0.033 ng/µl with a final concentration of 0.2 ng/µl for the entire pool. Five µl (1 ng) of the pooled DNA samples was arrayed on microtiter plates and subjected to gene-specific PCR.

PCR amplification was performed in 15 µl volumes containing 1 ng pooled DNA, 0.75× ExTaq buffer (Clonetech, Mountain View, Calif.), 1.1 mM additional MgCl2, 0.3 mM dNTPs, 0.3 µM primers, 0.009 U Ex-Taq DNA polymerase (Clonetech, Mountain View, Calif.), 0.02 units DyNAzyme II DNA Polymerase (Thermo Scientific), and if necessary 0.33M Polymer-Aide PCR Enhancer (Sigma-Aldrich®) PCR amplification was performed using an MJ Research® thermal cycler as follows: 95° C. for 2 minutes: 8 cycles of "touchdown PCR" (94° C. for 20 second, followed by annealing step starting at 70-68° C. for 30 seconds and decreasing 1° C. per cycle, then a temperature ramp of 0.5° C. per second to 72° C. followed by 72° C. for 1 minute); 25-45 cycles of 94° C. for 20 seconds, 63 or 65° C. for 30 seconds, ramp 0.5° C./sec to 72° C., 72° C. for 1-2 minutes; 72° C. for 8 minutes; 98° C. for 8 minutes; 80° C. for 20 seconds, 60 cycles of 80° C. for 7 seconds −0.3 degrees/cycle.

Primers for use in amplification of LPA-3 genes are shown in Table 4 below.

TABLE 4

Primers for LPA-3

| SEQ ID NO | Primer ID | PrImer Name | Primer Sequence |
|---|---|---|---|
| 7 | 4252 | Phytate-03g167800-F1 | CCAGCAAACAACACAACAGAGCAGCAAAG |
| 8 | 4255 | Phytate-03g167800-R1 | CTCCACGCATTTCCTCCAATTTCACTCTATATCTG |
| 9 | 4315 | Phytate-03g167800-F10 | GGAAGGAGGCAGCTTGTAATGCCGTATTT |
| 10 | 4260 | Phytate-03g167800-R4 | ACATGTTTCCTCATTGTATTTGTCTTGGCCTCTT |
| 11 | 4261 | Phytate-03g167800-F6 | GGGAAAGAGCGGATACATTGCAAAGTGC |
| 12 | 4263 | Phytate-03g167800-R5 | TGGATACCAAATTTAGCTCAGATGGAGGGTTATT |

Primers for use in amplification of LPA-19 genes are shown in Table 5 below.

TABLE 5

Primers for LPA-19 genes

| SEQ ID NO | Primer ID | Primer Name | Primer Sequence |
|---|---|---|---|
| 13 | 4411 | Phytate-19g169000-F3 | CTTCGTTGGCTTGGGCACTTCTCAAATC |
| 14 | 4414 | Phytate-19g169000-R4 | AGAAACCTCACTTTGAAATACCGGAGGGC |

Primers for use in amplification of LEC1 genes are shown in Table 6 below

TABLE 6

Primers for LEC1

| SEQ ID NO | Primer ID | Primer Name | Primer Sequence |
|---|---|---|---|
| 15 | 3197 | Lec02g_1_F1 | GAGGATGGATTTAAACCAGTCAGCACCGTAAGT |
| 16 | 3198 | Lec02g_1_R1 | GTTGCTGCTGTTCTTGTTTGCTCTGCGTTACT |

PCR products (2-4 µl) were digested in 96-well plates. 3 µl of a solution containing 6 mM HEPES [4-(2-hydroxyethyl)-1-piperazineethanesulfonic acid] (pH 7.0), 6 mM MgCl2, 6 mM NaCl, 0.012× Triton® X-100, 0.03 mg/ml of bovine serum albumin, 0.5× T-Digest Buffer [Advanced Analytical Technologies, Inc (AATI), Ames, Iowa], 0.912 U each of Surveyor® Endonuclease and Enhancer (Transgenomic®, Inc.), and 0.5× dsDNA Cleavage Enzyme (AATI, Ames, Iowa) was added to the PCR product. Digestion reactions were incubated at 45° C. for 45 minutes. The specific activity of the Surveyor enzyme was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 20 µl of Dilution Buffer E (AATI, Ames, Iowa) or 1×TE. The reactions were stored in the freezer until they were run on the Fragment Analyzer™ (AATI, Ames, Iowa) Capillary Electrophoresis System. Samples were run on the Fragment Analyzer™ utilizing the DNF-920-K 1000T Mutation Discovery Kit (AATI, Ames, Iowa) according to the manufacturer's protocol.

After electrophoresis, the assays were analyzed using PROSize® 2.0 Software (AATI, Ames, Iowa). The gel image showed sequence-specific pattern of background bands common to all 96 lanes. Rare events, such as mutations, create new bands that stand out above the background pattern. Plants with bands indicative of mutations of interest were evaluated by TILLING individual members of a pool mixed with wild type DNA and then sequencing individual PCR products.

Plants carrying mutations confirmed by sequencing were grown up as described above (e.g., the M2 plant was backcrossed or outcrossed twice in order to eliminate background mutations and self-pollinated in order to create a plant that was homozygous for the mutation).

Example 2: Identification of LPA3 and LPA19 Mutations

Identification of LPA-3 Mutation W328*

DNA from a soybean plant originating from seeds that were incubated in EMS was amplified using primers 4252 and 4255 (SEQ ID NOs: 7 and 8). The PCR amplification products were evaluated as described in Example 1. The electrophoresis gel image showed a fragment that stood out above the background pattern for the PCR amplification products. Therefore, it was likely that this fragment contained a heteroduplex created by a mutation in the Lpa3 sequence. Sequence analysis of this fragment showed the mutation was a G to A change at nucleotide 1124 of SEQ ID NO: 1. This mutation was associated with a change from tryptophan (W) to a stop codon at amino acid 328 of the LPA-3 protein shown in SEQ II) NO: 2 and is known as LPA-3(W328*).

Identification of LPA-3 Mutation Q612*

DNA from a soybean plant originating from seeds that were incubated in EMS was amplified using primers 4315 and 4260 (SEQ ID NOs. 9 and 10). The PCR amplification products were evaluated as described in Example 1. The electrophoresis gel image showed a fragment that stood out above the background pattern for the PCR amplification products. Therefore, it was likely that this fragment contained a heteroduplex created by a mutation in the Lpa3 sequence. Sequence analysis of this fragment showed the mutation was a C to T change at nucleotide 1934 of SEQ ID NO: 1. This mutation was associated with a change from glutamine (Q) to a stop codon at amino acid 612 of the LPA-3 protein shown in SEQ ID NO:2 and is known as LPA-3(Q612*).

Identification of LPA-3 Mutation G1330D

DNA from a soybean plant originating from seeds that were incubated in EMS was amplified using primers 4261 and 4263 (SEQ ID NOs: 11 and 12). The PCR amplification products were evaluated as described in Example 1. The electrophoresis gel image showed a fragment that stood out above the background pattern for the PCR amplification products. Therefore, it was likely that this fragment contained a heteroduplex created by a mutation in the Lpa3 sequence. Sequence analysis of this fragment showed the mutation was a G to A change at nucleotide 5681 in an ATP binding site encoding region of SEQ ID NO: 1. This mutation was associated with a change from glycine (G) to aspartate (D) at amino acid 1330 in the ATP binding site of the LPA-3 protein shown in SEQ ID NO: 2 and is known as LPA-3(G1330D).

Identification of LPA-19 Mutation Q438*

DNA from a soybean plant originating from seeds that were incubated in EMS was amplified using primers 4411 and 4414 (SEQ ID NOs: 13 and 14) The PCR amplification products were evaluated as described in Example 1. The electrophoresis gel image showed a fragment that stood out above the background pattern for the PCR amplification products. Therefore, it was likely that this fragment contained a heteroduplex created by a mutation in the LPA-19 sequence. Sequence analysis of this fragment showed the mutation was a C to T change at nucleotide 1412 of SEQ ID NO: 3. This mutation was associated with a change from glutamine (Q) to a stop codon at amino acid 438 of the LPA-19 protein shown in SEQ ID NO:4 and is known as LPA-19(Q438*).

Identification of LPA-19 Mutation G682S

DNA from a soybean plant originating from seeds that were incubated in EMS was amplified using primers 4411 and 4414 (SEQ ID NOs: 13 and 14). The PCR amplification products were evaluated as described in Example 1. The electrophoresis gel image showed a fragment that stood out above the background pattern for the PCR amplification products. Therefore, it was likely that this fragment contained a heteroduplex created by a mutation in the LPA-19 sequence. Sequence analysis of this fragment showed the mutation was a G to A change at nucleotide 2144 in an ATP binding site encoding region of SEQ ID NO: 3. This mutation was associated with a change from glycine (G) to a serine (S) at amino acid 682 in the first ATP binding site of LPA-19 protein shown in SEQ ID NO. 4 and is known as LPA-19(G682S).

Example 3: Characterization of LPA-3 and LPA-19 Lines

Plants carrying mutations confirmed by sequencing were grown and used in crosses to generate additional mutant lines. The M2 plant is backcrossed or outcrossed multiple times in order to eliminate background mutations and self-pollinated to create a plant that is homozygous for the mutation. Homozygous mutant lines are crossed to homozygous lines having mutations in a different allele to generate lines with mutations in both LPA genes. Crosses were made using lines homozygous for LPA-3 and LPA-19 mutants as shown in Table 7 below. The resulting lines were crossed and selfed to obtain lines that are homozygous for the noted mutations in the LPA-3 and LPA-19 genes.

TABLE 7

Crosses were made using lines homozygous for mutations in LPA-3 and LPA-19

| Cross | LPA-3 Mutant | LPA-19 Mutant |
|---|---|---|
| A1 × A2 | Q612* | G682S |
| 1 × A2 | W328* | G682S |
| 1 × 3 | W328* | Q438* |
| 2 × 3 | G1330D | Q438* |

Phytate content in homozygous LPA-3/LPA-19 double mutants was determined using standard analytical methods (Covance Laboratories) and compared to phytate levels in seeds of the non-mutagenized Jocketa mother line or to WT plants that segregated in the breeding process. Results are shown in Table 8 below. Phytate levels were reduced by at least 50% in all four of the resulting lines, with some lines having phytate levels reduced by more than 80% as compared to the control.

TABLE 8

Phytate content in homozygous LPA-3/LPA-19 double mutants

| Plant Line | Phytate (mg/g) | % Reduction vs. Control |
|---|---|---|
| Jocketa | 20.4 | |
| Q612* LPA-3 × G682S LPA-19 (ATP) | 7.8 | 62% |
| WT phytate | 16.3 | |
| W328* LPA-3 × G682S LPA-19 (ATP) | 7.8 | 52% |
| WT phytate | 15.2 | |
| W328* LPA-3 × Q438* LPA-19 | 1.9 | 88% |
| WT phytate | 21.7 | |
| Q438* LPA-19 × G1330D LPA-3 (ATP) | 2.4 | 89% |

The above demonstrates reductions of phytate levels in LPA-3/LPA-19 homozygous mutants. Soybean seeds from plants having LPA-3 mutations W328* of SEQ ID NO. 2 and G1330D of SEQ ID NO. 2 and LPA-19 mutations Q438* of SEQ ID NO. 4 demonstrate phytate seed content reductions of greater than 86%.

Additional crosses can be made to generate soybean mutant lines with mutations G1330D LPA-3 of SEQ ID NO. 2 and G682S LPA-19 of SEQ ID NO. 4 to test the effect of double homozygous mutations where the mutations are in encoding regions for ATP binding sites in LPA-3 and LPA-19.

Example 4: Identification and Characterization of a LEC1 Mutation

Identification of LEC1-Mutation L228*

DNA from a soybean plant originating from seeds that were incubated in EMS was amplified using primers 3197 and 3198 (SEQ ID NOs. 15 and 16). The PCR amplification products were evaluated as described in Example 1. The electrophoresis gel image showed a fragment that stood out above the background pattern for the PCR amplification products. Therefore, it was likely that this fragment contained a heteroduplex created by a mutation in the LEC1 sequence. Sequence analysis of this fragment showed the mutation was a T to A change at nucleotide 1393 of SEQ ID NO: 5. This mutation was associated with a change from leucine (L) to a stop codon at amino acid 228 of the LEC1 protein shown in SEQ ID NO: 6 and is known as LEC1 (L228*).

Soybean plants homozygous for the LEC1 mutant described above are generated and the lectin content of harvested seeds is determined over two seasons. Results are shown in Table 9 below and demonstrate that no lectin can be detected in seeds of the homozygous LEC1 mutant.

TABLE 9

Lectin content of soybean plants homozygous for the LEC1 mutant

| | Spring | Fall |
|---|---|---|
| Line | Lectin Content (mg/g) | |
| LEC1 - L228* | <0.375 | <0.375* |
| Non-mutagenized mother line | 4.9 | 3.2 |

*lowest detectable level by the method used

Harvest results from field trials also indicate that the undetectable level of lectin in the L228* LEC1 mutant did not have a negative impact on seed yield as compared to seed yield of the non-mutagenized mother line.

Example 5: Low Phytate and Low/No Lectin Mutants

Soybean plants homozygous for the no lectin LEC1 L228*mutation and the LPA-3/LPA-19 double mutants described above are generated by crossing and selfing with the low lectin homozygous line and the low phytate double mutant homozygous lines resulting in the following lines:
  Q612* LPA-3/G682S LPA-19/L228* LEC1
  W328* LPA-3/Q438* LPA-19/L228* LEC1
  Q438* LPA-19/G1330D LPA-3/L228* LEC1
  W328* LPA-3/G682S LPA-19/L228* LEC1

Phytate and lectin contents of harvested seeds of Q612* LPA-3/G682S LPA-19/L228* LEC1 were determined using standard analytical methods (Covance Laboratories) and shown in Table 10 below.

TABLE 10

Phytate and lectin contents of harvested seeds of Q612* LPA-3/G682S LPA-19/L228* LEC1

| Line | Phytate Content (mg/g) | Phytate % Reduction vs. Control (%) | Lectin Content (mg/g) | Lectin % Reduction vs. Control |
|---|---|---|---|---|
| Q612* LPA-3/G682S LPA-19/L228* LEC1 | 4.4 | 46 | <0.375* | >92 |
| WT phytate segregant LEC- | 8.1 | | <0.375 | >92 |

*lowest detectable level by the method used

The above demonstrates reduced levels of phytate and lectin in seeds of soybean plants having homozygous mutations in LPA-3, LPA-19 and LEC1, and reduced levels of lectin in wildtype phytate segregants from the breeding cross. Seed yield analysis of greenhouse generated and field grown seed indicates that the low phytate phenotype and low lectin phenotypes did not have a negative impact on seed yield.

Example 6: Reduced Antinutrient Soybean Meal in Aquaculture

Soybean meal prepared from no lectin mutant L228* and Lec+ wild type seeds is used in a fish feeding study to determine the effect of the reduction in antinutrients on fish growth, as compared to the reduction in fish growth fed with wild type soybean meal. Feed containing 50% soybean meal and 50% fish protein (artemia and rotifers) was prepared and used in a feeding study of zebrafish as a model species as follows.

Soybean meal having reduced or wild type levels of lectin was prepared as granules and analyzed to determine fat, protein and lectin content. Results of the component analysis are shown in Table 11 below.

TABLE 11

| Content of granules prepared from soybean meal | | |
|---|---|---|
| | Lectin (−) | Lectin (+) |
| Fat | 19.70% | 19.10% |
| Protein | 36.00% | 36.60% |
| Lectin | <0.375 mg/g | 2.38 mg/g |

From 5 to 34 days post fertilization (dpf), all fish were feed a normal diet (artemia and rotifers). At 35 dpf females were sorted based on expression of Tg(ziwi:egfp) to enrich for females. Sixty fish (mostly female) were placed into a 9 L tank and fed 2× per day using an auto-feeder (food measured by volume). At 58 dpf (today) fish were sexed and only the females were weighed. It was noted during the study that fish were able to avoid the soy granules due to their large size, but positive effects of the reduced lectin soybean meal were observed as described below. Future trials will use smaller soy granules and are expected to demonstrate even better performance in aquaculture.

Fish fed a 50% soybean meal diet prepared using a no lectin mutant weighed on average 72% of the controls while fish fed a 50% soybean meal diet prepared from lectin+ wildtype seeds weighed on average 62% of controls. Thus, use of a reduced, or "no lectin" soybean plant for preparation of fish meal containing 50% soybean content adds 16% weight gain.

These results demonstrate that soybean meal from lectin (−) mutants is a better feed for use in aquaculture than soybean meal from lectin(+) wildtype soybean seeds.

Additional feeding studies can be conducted with soybean meal having reduced levels of phytate and reduced levels of lectin for aquaculture and other animals.

The above examples are provided to illustrate the invention but not limit its scope. Other variants of the invention will be readily apparent to one of ordinary skill in the art and are encompassed by the appended claims and all their equivalents. The examples above used TILLING technology to create and identify mutations in one or more LPA-3, LPA-19 or LEC1 genes of soybean that decrease phytate (LPA-3, LPA-19) or lectin (LEC1) in soybean seeds, but one of ordinary skill in the art would understand that other methods such as targeted mutagenesis (also known as site-directed mutagenesis, site-specific mutagenesis, oligonucle-otide-directed mutagenesis or genome editing) can be used to create mutations, including the useful mutations described herein, in the corresponding loci in other soybean varieties (see for example Zhang et al., PNAS 107(26):12028-12033, 2010; Saika et al., Plant Physiology 156:1269-1277, 2011). All publications, patents, and patent applications cited herein are hereby incorporated by reference.

```
Glyma.03g167800_cDNA LPA3
                                                       SEQ ID NO: 1
ATGGCCGTCGATGAAATTGAAATCTTGTCTCCTACGTTTTCTTCTTCGGGATCGTTTGAGACCC

TTTGGAGTGCGATCCTCGGATTGCCTTTGTTGAACTGGTGGCAATTTGTGCCAACTTGACACT

GTCTCTTCTCTTTCTCTTCGTTGTTTCGGCGAGGAAGGTGCTTGTGTGTAGGGAGAGGAGTA

AGATTTGGTAAGGAGAACATAACCGGCAATGCCAGCCCCGGTTGTGTTAGTGTTGATTTGGAAA

CACGTGACGTCGTTCGGATTGAAACGTGGTTCAAGTTGTCGGTGTTGTCTTGTTTGTATGTTCT

GTTGGTGCAAGTTTTGCTCTTGGGGTTTGATGGGGTTGCTTTGATTAGAGGAAGGGATTTGGAT

GTGGATTTGGATTTGGGTTTGGCTCTTCTTTCTGTGCCTCTTGTGCAGGGTTTAGCTTGGGTTG

TGTTGAGCTTCTCGGCTTTGCAATGCAAGTTCAAGGCGTCTGAGAGGTTTCCAATTTTGCTCAG

ACTTTGGTGGGTTATGCTGTTTGGTATTTGTTTGTGTGGTTTGTATGTTGATGGTAAGGGGGTT

TGGATGGAGGGTTCCAAGCACCTGCGGTCTCATGTTGTGGCGAATTTCACCATCACTCCTGCTC

TTGCCTTTTTGTGTATTGTGGCAATTAGGGGTGTTACTGGTATAAAGGTTTTTAGGAATTCCGA

GGAGCACCAGCCATTGCTTGTTGAGGAGGAACCGGGGTGTCTCAAGGTTACTCCTTATACTGAT

GCCGGACTTTTTAGCTTGGCCACTTTGTCTTGGTTGAATCCACTTCTTTCCATAGGGGCAAAAA

GGCCGCTTGAGCTTAAGGACATTCCCCTTGTTGCGGCGAAAGACCGATCCAAGACAAATTATAA

GGTTTTGAATTCTAATTGGGAGAGGTTGAAGGCTGAAAACCAATCCGAGCAGCCTTCCTTGGCT

TGGGCACTTCTCAAGTCCTTCTGGAAGGAGGCAGCTTGTAATGCCGTATTTGCTGGTGTCACTA

CTCTTGTCTCGTATGTCGGTCCGTACATGATAAGTTACTTTGTTGATTACTTGGTTGGCAAAGA

GATTTTCCCACATGAGGGGTATGTCCTTGCAGGGGTATTCTTTGTGGCAAAGCTTGTGGAGACC

TTTACTACTAGGCAGTGGTATCTTGGGGTGGACATCTTGGGTATGCATGTTAGGTCGGCTCTAA

CTGCAATGGTATATCGAAAGGGGCTAAGGATATCAAGCTTGGCCAAGCAAAGTCACACGAGTGG
```

-continued

```
GGAGGTTGTTAACTACATGGCTATTGATGTTCAGAGGGTAGGGGACTACTCTTGGTATCTTCAT

GACATGTGGATGCTTCCTCTGCAGATTGTTCTTGCCCTTGCAATTTTGTATAAGAATGTTGGAA

TTGCTGCTATTGCAACACTGATTGCTACAATAATTTCCATCGTCGTCACTGTTCCTATTGCCAG

GGTCCAAGAAAATTATCAAGACAAATTAATGGCTGCTAAGGATGAAAGGATGAGAAAAACATCT

GAGTGCCTGAGGAATATGAGGATTCTCAAACTTCAAGCTTGGGAGGACAGATATAGAGTGAAAT

TGGAGGAAATGCGTGGAGTAGAGTTCAAGTGGCTTCGGAAAGCCCTCTATTCTCAGGCTTTCAT

AACTTTCATATTCTGGAGCTCCCCTATATTGTTTCGGCGGTCACTTTTGCTACTTCCATATTG

TTGGGTGGTCAGCTGACTGCTGGTGGTGTACTTTCTGCTCTGGCTACTTTCAGGATCCTGCAAG

AACCTTTGAGGAATTTTCCGGACTTGGTGTCAACAATGGCTCAGACAAAGGTTTCTCTTGACCG

ATTATCTGGTTTCCTGCTGGAGGAGGAATTGCAGGAAGATGCAACTATTGTCTTGCCACAAGGC

ATTACTAACATTGCTATAGAAATTAAGGATGGTATCTTCTGTTGGGACCCTTCTTCATCTTTTA

GGCCTACCCTATCAGGGATAAGTATGAAAGTTGAAAGAAGGATGCGCGTGGCTGTTTGTGGTAT

GGTTGGTTCAGGGAAATCGAGTTTTCTTTCGTGCATCCTTGGAGAGATTCCTAAACTTTCTGGT

GAAGTTAGAGTGTGTGGCTCTTCTGCTTATGTCTCCCAATCAGCGTGGATACAATCAGGAACTA

TAGAAGAAAATATCCTCTTTGGAAGCCCAATGGACAAAGCAAAGTACAAGAATGTTCTTCATGC

TTGTTCACTGAAAAAGGACCTAGAACTTTTCTCACATGGTGATCAGACAATTATTGGGGATAGA

GGTATAAACCTGAGTGGTGGCCAGAAGCAGCGGGTTCAGCTTGCACGAGCACTCTACCAAGATG

CTGATATTTATCTTCTGGATGATCCCTTCAGTGCAGTTGATGCTCACACTGGATCAGACTTGTT

TAGGGAGTATATATTGACAGCACTTGCAGATAAAACAGTCATTTTTGTGACCCATCAAGTTGAA

TTTCTTCCCGCTGCTGATTTGATTCTGGTTCTTAAAGAAGGATGCATCATACAGTCAGGAAAGT

ATGATGATCTTTTACAAGCAGGAACAGATTTTAATACTCTGGTTTCAGCTCACCATGAAGCCAT

AGAGGCTATGGATATCCCTACTCACTCCTCTGAAGAGTCAGATGAAAATTTATCCCTGGAGGCA

TCTGTTATGACCAGTAAGAAATCCATTTGTTCAGCAAATGATATAGACAGTTTAGCAAAGGAAG

TGCAAGAGGGATCATCTATTTCAGATCAAAAAGCAATTAAAGAGAAGAAGAAGAAAGCAAAACG

ATCGAGAAAGAAACAGCTTGTTCAGGAAGAGGAGAGGATTAGAGGTAGAGTCAGCATGAAGGTG

TATCTTTCATACATGGCAGCAGCATATAAAGGCTTATTGATTCCACTCATAATCATTGCACAAA

CATTATTTCAGTTCCTTCAGATTGCAAGCAATTGGTGGATGGCTTGGGCTAACCCTCAAACAGA

AGGAGACCTGCCCAAAGTAACTCCCTCAGTTCTTCTTCTTGTTTATATGGCCCTTGCTTTTGGC

AGCTCATGGTTTATATTTGTAAGGGCTGTTCTGGTGGCTACATTTGGTCTTGCAGCTGCCCAGA

AGCTATTTTTGAAAATGCTTAGAAGTGTTTTCCATGCACCAATGTCTTTCTTTGACTCTACACC

AGCTGGAAGGATCTTGAATCGGGTATCAATTGATCAAAGTGTTGTGGATCTTGACATTCCTTTT

AGACTTGGTGGATTTGCTTCAACTACAATACAGCTTATTGGTATTGTTGGTGTAATGACAGAAG

TTACATGGCAAGTTTTGCTCTTAGTTGTCCCAATGGCTGTTGCTTGTTTGTGGATGCAGAAATA

CTACATGGCTTCCTCAAGGGAACTGGTTCGTATTGTTAGCATACAGAAGTCTCCAATTATACAT

CTTTTTGGTGAATCAATTGCTGGAGCATCCACCATCAGGGGTTTTGGACAAGAAAAAAGGTTCA

TGAAGCGGAACCTCTATCTTCTTGATTGCTTTGCACGACCATTCTTCTGCAGTCTTTCTGCAAT

TGAGTGGCTCTGCCTGCGGATGGAGTTACTGTCAACCTTTGTATTTGCTTTCTGTATGGTATTA

CTTGTGAGTTTTCCTCGTGGAAGTATCGACCCCAGCATGGCTGGACTTGCTGTGACATATGGCC

TGAATTTAAATGCACGCCTATCACGGTGGATACTCAGCTTTTGCAAGCTTGAAAATAAAATTAT

ATCTATTGAGAGAATTTATCAGTACAGCCAAATTCCTAGTGAAGCACCCACAATTATTGAAGAT

TCTCGCCCTCCATTCTCATGGCCAGAAAATGGGACAATTGAAATAATTGATTTGAAGGTCCGTT
```

-continued

```
ACAAGGAGAATCTTCCTATGGTGCTTCATGGAGTAACATGCACATTTCCAGGTGGAAAGAAGAT

TGGAATAGTTGGACGTACTGGCAGTGGAAAATCTACTTTAATTCAGGCGTTATTTCGATTGATT

GAACCAGCAAGTGGGAGTATCCTTATAGACAACATTAATATTTCAGAGATTGGCCTTCATGACC

TTCGAAGCCATCTCAGTATCATACCTCAAGATCCAACCTTATTTGAAGGTACCATTCGAGGCAA

TCTTGATCCTCTGGATGAGCACTCAGATAAAGAGATTTGGGAGGCACTTGATAAGTCTCAGCTT

GGAGAGGTTATCCGTGAGAAAGGACAACAGCTTGACACACCAGTTCTAGAAAATGGAGATAATT

GGAGTGTAGGACAGCGACAACTTGTTGCTCTGGGCCGAGCTCTGCTGCAGCAGTCAAGAATACT

TGTACTGGATGAAGCAACAGCATCAGTTGATACTGCCACGGATAATCTTATCCAGAAGATTATC

CGAAGTGAGTTCAAAGACTGCACTGTTTGCACCATTGCACATCGAATACCTACTGTCATTGACA

GTGATCTAGTTCTTGTGCTCAGTGATGGTCTAGTCGCAGAGTTCGACACTCCTTCAAGACTATT

AGAGGATAAGTCATCCGTGTTTCTGAAGTTGGTGACCGAGTATTCATCACGTTCAAGTGGCATA

CCAGACTTTTAG
```

Glyma.03g167800_prt LPA3

SEQ ID NO: 2

```
MAVDEIEILSPTFSSSGSFETLWSAILGLPLLELVAICANLTLSLLFLFVVSARKVLVCVGRGV

RFGKENITGNASPGCVSVDLETRDVVRIETWFKLSVLSCLYVLLVQVLLLGFDGVALIRGRDLD

VDLDLGLALLSVPLVQGLAWVVLSFSALQCKFKASERFPILLRLWWVMLFGICLCGLYVDGKGV

WMEGSKHLRSHVVANFTITPALAFLCIVAIRGVTGIKVFRNSEEHQPLLVEEEPGCLKVTPYTD

AGLFSLATLSWLNPLLSIGAKRPLELKDIPLVAAKDRSKTNYKVLNSNWERLKAENQSEQPSLA

WALLKSFWKEAACNAVFAGVTTLVSYVGPYMISYFVDYLVGKETFPHEGYVLAGVFFVAKLVET

FTTRQWYLGVDILGMHVRSALTAMVYRKGLRISSLAKQSHTSGEVVNYMAIDVQRVGDYSWYLH

DMWMLPLQIVLALAILYKNVGIAAIATLIATIISIVVTVPIARVQENYQDKLMAAKDERMRKTS

ECLRNMRILKLQAWEDRYRVKLEEMRGVEFKWLRKALYSQAFITFIFWSSPIFVSAVTFATSIL

LGGQLTAGGVLSALATFRILQEPLRNFPDLVSTMAQTKVSLDRLSGFLLEEELQEDATIVLPQG

ITNIAIEIKDGIFCWDPSSSFRPTLSGISMKVERRMRVAVCGMVGSGKSSFLSCILGEIPKLSG

EVRVCGSSAYVSQSAWIQSGTIEENILFGSPMDKAKYKNVLHACSLKKDLELFSHGDQTIIGDR

GINLSGGQKQRVQLARALYQDADIYLLDDPFSAVDAHTGSDLFREYILTALADKTVIFVTHQVE

FLPAADLILVLKEGCIIQSGKYDDLLQAGTDFNTLVSAHHEAIEAMDIPTHSSEESDENLSLEA

SVMTSKKSICSANDIDSLAKEVQEGSSISDQKAIKEKKKKAKRSRKKQLVQEEERIRGRVSMKV

YLSYMAAAYKGLLIPLIIAQTLFQFLQIASNWWMAWANPQTEGDLPKVTPSVLLLVYMALAFG

SSWFIFVRAVLVATFGLAAAQKLFLKMLRSVFHAPMSFFDSTPAGRTLNRVSIDQSVVDLDIPF

RLGGFASTTTQLIGIVGVMTEVTWQVLLLVVPMAVACLWMQKYYMASSRELVRIVSIQKSPIIH

LFGESIAGASTIRGFGQEKRFMKRNLYLLDCFARPFFCSLSAIEWLCLRMELLSTFVFAFCMVL

LVSFPRGSIDPSMAGLAVTYGLNLNARLSRWILSFCKLENKIISIERIYQYSQIPSEAPTIIED

SRPPFSWPENGTIEIIDLKVRYKENLPMVLHGVTCTFPGGKKIGIVGRTGSGKSTLIQALFRLI

EPASGSILIDNINISEIGLHDLRSHLSIIPQDPTLFEGTIRGNLDPLDEHSDKEIWEALDKSQL

GEVIREKGQQLDTPVLENGDNWSVGQRQLVALGRALLQQSRILVLDEATASVDTATDNLTQKII

RSEFKDCTVCTIAHRIPTVIDSDLVLVLSDGLVAEFDTPSRLLEDKSSVFLKLVTEYSSRSSGI

PDF*
```

Glyma.19g169000_cDNA LPA19
SEQ ID NO: 3

```
ATGGCCGTCGATGAAATTGAAATATTGTCTTCGACGTTGTTTTCTTCTTCTTCGGGATCGT
TTGAGATCCTTTGGAGTGCGATCCTCGGATTGCCTTTGTTGGAACTGGTGGCAATCTGTGCCAA
CCTGACACTGTTTATTCTCTTTCTCGTCGTTGTTTCGGCGAGGAAGGTGCTTGTGTGTATGG
GGAGGAGTTAGATTCGGTAAGGAGAACGGAACCGGCAATGCCAGCCCCGGTTGTGTTAGTGTTG
ATTTGGAAACACGTGACATTCGGATTGAAACGTGGTTCAAGTTGTCGGTGTTGTCTTGTTTCTA
TGTTCTGTTGGTGCAAGTTTTGGTCTTGGGGTTTGATGGGGTTGCTTTGATTAGAGGAAGGGAT
TTGGATTTGGATTTGGGTTTGGCTCTTCTTTCTGTGCCTCTTGTGCAGGGTTTAGCTTGGGTTG
TGTTGAGCTTCTCGGCTTTGCAATGCAAATTCAAGGCGTGTGAGAGGTTTCCAGTTTTGCTTAG
AGTTTGGTTATTTGTGGTGTTCGTTATTTGTTTGTGTGGTTTGTATGTTGATGGAAGGGGGGTT
TGGATGGAAGGTTCCAAGCACCTGCGTTCTCATGTTGTGGCGAATTTCGCCGTCACTCCTGCTC
TTGCCTTTTTGTGTATTGTGGCAATTAGGGGTGTTACTGGTATAAAGGTTTTTAGGAGTTCTGA
GGAGCAACAGCCATTGCTTGTTGATGAGGATCCCGGGTGTCTCAAGGTTACTCCTTATAGTGAT
GCTGGACTTTTTAGCTTGGCCATTTTGTCTTGGTTGAATCCACTTCTTTCCATTGGGGCAAAAA
GGCCGCTTGAGCTTAAGGACATTCCCCTTGTTGCGCCGAAAGACCGATCCAAGACAAATTATAA
GGTTTTGAATTCTAATTGGGAGAGGTTGAAGGCTGAAAAACCTATCCGGGCAGCCTTCGTTGGCT
TGGGCACTTCTCAAATCCTTCTGGAAGGAGGCGGCTTGTAACGCTGTGTTTGCTGGTGTCACTA
CTCTTGTCTCGTATGTTGGTCCATATATGATAAGTTACTTTGTTGATTACTTGGTTGGCAAAGA
GATTTTCCCACATGAGGGGTATGTCCTTGCAGGGGTATTCTTTGTGGCAAAGCTTGTGGAGACC
TTTACTACTAGGCAGTGGTATCTTGGGGTGGATATCTTGGGTATGCATGTTAGGTCGGCTCTAA
CTGCAATGGTATATCGAAAGGGGCTAAGGATATCAAGCTTGGCCAAGCAAAGTCACACGAGCGG
GGAGGTTGTTAACTACATGGCTATTGATGTTCAGAGGGTAGGGGACTACTCTTGGTATCTTCAT
GACATGTGGATGCTTCCTCTGCAGATTGTTCTTGCCCTTGCGATTTTGTATAAGAATGTTGGAA
TTGCTTCTATTGCAACACTGATTGCTACAATAATTTCCATCGCGGTCACTGTTCCTATTGCCAG
GATCCAAGAAAATTATCAAGACAAATTAATGGCTGCTAAGGATGAAAGGATGAGAAAAACATCT
GAGTGCCTGAGGAATATGAGGATTCTCAAACTTCAAGCTTGGGAGGATAGATATAGAGTGAAAT
TGGAGGAAATGCGAGGAGTAGAGTTCAAGTGGCTTCGGAAAGCTCTCTATTCTCAGGCTTTCAT
AACTTTCATATTCTGGAGCTCCCCTATATTTGTTTCAGCAGTCACTTTTGGTACTTCCATATTG
TTGGGTGGTCAGCTGACTGCTGGTGGTGTACTTTCTGCTTTGGCTACTTTCAGGATCCTGCAAG
AACCTTTGAGGAATTTTCCGGACTTGGTGTCAACAATGGCTCAGACAAAGGTTTCTCTTGACCG
ATTATCTGGTTTCCTGCTGGAGGAGGAATTGCAGGAAGATGCAACTATTGTCTTGCCACAAGGC
ATTACTAACATTGCTATAGAAATTAAGGGTGGTGTCTTCTGTTGGGACCCTTCTTCATCTTCTA
GACCTACCCTATCAGGGATAAGTATGAAAGTTGAAAGAAGGATGCGTGTGGCTGTTTGTGGTAT
GGTTGGTTCAGGGAAATCAAGTTTTCTTTTGTGCATCCTTGGAGAGATTCCTAAAATTTCTGGT
GAAGTTAGAGTGTGTGGCTCTTCTGCATATGTCTCCCAATCAGCATGGATACAATCAGGAACTA
TAGAAGAAAATATCCTCTTTGGAAGCCCAATGGACAAAGCAAAGTACAAGAATGTTCTTCATGC
TTGTTCACTGAAAAAGGACCTAGAACTTTTCTCACATGGTGATCTTACAATTATTGGGGATAGA
GGTATAAACCTGAGTGGTGGCCAGAAGCAGCGGGTTCAGCTGGCTCGGGCACTCTACCAAGATG
CTGATATTTATCTTCTTGATGATCCCTTCAGTGCAGTTGATGCTCACACTGGATCAGACTTGTT
TAGGGAGTATATATTGACAGCACTTGCAGATAAAACAGTCATTTATGTGACCCATCAAGTTGAA
```

-continued

```
TTTCTTCCTGCTGCTGATTTGATATTGGTTCTCAAAGAAGGATGCATCATACAGTCAGGAAAGT
ATGACGATCTTTTACAAGCAGGAACAGATTTTAATACTCTGGTTTCAGCTCACAATGAAGCCAT
AGAGGCCATGGATATCCCTACTCACTCTGAAGATTCAGATGAAAATTTATCCCTGGAGGCATGT
GTTATGACCAGTAAGAAATCCATTTGTTCTGCAAATGATATAGACAGTTTGGCAAAGGAAGTGC
AAGAGGGATCATCTATTTCAGATCAAAAAGCAATTAAAGAAGAAGAAAGCAAAACGATCGAG
AAAGAAACAGCTTGTTCAGGAAGAGGAGAGGATTAGAGGTAGAGTCAGCATGAAGGTGTATTTG
TCATACATGGCAGCAGCATATAAAGGCTTATTGATTCCACTCATAATCATTGCACAAACATTAT
TTCAGTTCCTTCAGATTGCTAGCAATTGGTGGATGGCTTGGGCTAATCCTCAAACAGAAGGAGA
CCTGCCCAAAGTAACTCCCTCAGTTCTTCTTCTTGTTTATATGGCCCTTGCTTTTGGCAGCTCA
TGGTTTATATTTGTAAGGGCTGTTCTGGTGGCTACGTTTGGTCTTGCAGCTGCACAGAAGCTAT
TTTTGAAAATGCTTAGAAGTGTTTTCCATGCACCAATGTCTTTCTTTGACTCTACACCAGCTGG
AAGGATTTTGAATCGGGTATCAATTGATCAAAGTGTTGTGGATCTTGACATTCCTTTTAGACTT
GGTGGGTTTGCTTCAACAACAATACAGCTTATTGGTATTGTTGGTGTAATGACAGAAGTTACGT
GGCAAGTTTTGCTCTTAGTTGTCCCAATGGCTGTTGCTTGTTTGTGGATGCAGAAATACTACAT
GGCTTCCTCAAGGGAACTGGTTCGAATTGTTAGCATCCAGAAGTCTCCAATTATACATCTTTTT
GGTGAATCTATTGCTGGAGCATCCACCATCAGGGGTTTTGGACAAGAAAAAGGTTCATGAAGC
GAAACCTCTATCTTCTTGATTGCTTTGCACGACCATTCTTCTGCAGTCTTTCTGCAATTGAGTG
GCTCTGCCTGCGGATGGAGTTACTGTCAACCTTTGTATTTGCTTTCTGTATGGTATTACTTGTG
AGTTTTCCTCGTGGAAGTATCGACCCCAGCATGGCTGGACTTGCTGTGACATATGGCCTGAATT
TAAATGCACGTCTATCACGGTGGATACTCAGCTTTTGCAAACTTGAAAATAAAATTATATCTAT
TGAGAGAATTTATCAGTACAGCCAAATTCCTAGTGAAGCACCCACAGTTATTGAAGATTATCGC
CCTCCATCCTCATGGCCTGAAAATGGGACAATTGAAATAATTGATTTGAAGATTCGTTACAAGG
AGAATCTTCCTTTGGTGCTTTATGGAGTAACATGCACATTTCCTGGTGGAAAGAAGATTGGAAT
AGTAGGACGTACTGGCAGTGGAAAATCTACTTTAATTCAGGCGTTATTTCGATTGATTGAACCA
ACAAGTGGGAGTATCCTTATAGACAACATTAATATTTCAGAGATTGGCCTTCATGACCTTCGAA
GCCATCTCAGTATCATACCACAAGATCCAACCTTATTTGAAGGTACCATTCGAGGCAATCTTGA
TCCTCTGGATGAGCACTCAGATAAAGAGATTTGGGAGGCACTTGATAAGTCTCAGCTTGGAGAG
GTTATCCGTGAGAAAGGACAACAGCTTGATACGCCAGTTCTAGAAAATGGAGATAATTGGAGTG
TAGGACAGCGACAACTTGTTGCTCTGGGCCGAGCTCTGCTGCAGCAGTCAAGAATACTTGTACT
AGATGAAGCAACAGCATCAGTTGATACCGCCACAGATAATCTTATACAGAAGATTATCCGAAGT
GAGTTCAAAGAATGCACTGTTTGCACCATTGCACATCGAATACCTACTGTCATTGACAGTGATC
TAGTTCTTGTGCTCAGTGATGGTCGAGTTGCAGAGTTCAACACTCCTTCAAGACTATTAGAGGA
TAAGTCATCCATGTTTCTGAAGCTGGTGACTGAGTACTCATCACGTTCAAGTGGCATACCAGAC
TTTTAG
```

Glyma.19g169000_PRT LPA19

SEQ ID NO: 4

```
MAVDEIETLSSTLFSSSSSGSFEILWSAILGLPLLELVAICANLTLFILFLVVVSARKVLVCVW
GGVRFGKENGTGNASPGCVSVDLETRDIRIETWFKLSVLSCFYVLLVQVLVLGFDGVALIRGRD
LDLDLGLALLSVPLVQGLAWVVLSFSALQCKFKACERFPVLLRVWLFVVFVICLCGLYVDGRGV
WMEGSKHLRSHVVANFAVTPALAFLCIVAIRGVTGIKVFRSSEEQQPLLVDEDPGCLKVTPYSD
AGLFSLAILSWLNPLLSIGAKRPLELKDIPLVAPKDRSKTNYKVLNSNWERLKAENLSGQPSLA
WALLKSFWKEAACNAVFAGVTTLVSYVGPYMISYFVDYLVGKEIFPHEGYVLAGVFFVAKLVET
```

-continued

FTTRQWYLGVDILGMHVRSALTAMVYRKGLRISSLAKQSHTSGEVVNYMAIDVQRVGDYSWYLH

DMWMLPLQIVLALAILYKNVGIASIATLIATIISIAVTVPIARTQENYQDKLMAAKDERMRKTS

ECLRNMRILKLQAWEDRYRVKLEEMRGVEFKWLRKALYSQAFITFIFWSSPIFVSAVTFGTSIL

LGGQLTAGGVLSALATFRILQEPLRNFPDLVSTMAQTKVSLDRLSGFLLEEELQEDATIVLPQG

ITNIAIEIKGGVFCWDPSSSSRPTLSGISMKVERRMRVAVCGMVGSGKSSFLLCILGEIPKISG

EVRVCGSSAYVSQSAWIQSGTIEENILFGSPMDKAKYKNVLHACSLKKDLELFSHGDLTIIGDR

GINLSGGQKQRVQLARALYQDADIYLLDDPFSAVDAHTGSDLFREYILTALADKTVIYVTHQVE

FLPAADLILVLKEGCIIQSGKYDDLLQAGTDFNTLVSAHNEAIEAMDIPTHSEDSDENLSLEAC

VMTSKKSICSANDIDSLAKEVQEGSSISDQKAIKEKKKAKRSRKKQLVQEEERIRGRVSMKVYL

SYMAAAYKGLLIPLIIIAQTLFQFLQIASNWWMAWANPQTEGDLPKVTPSVLLLVYMALAFGSS

WFTFVRAVLVATFGLAAAQKLFLKMLRSVFHAPMSFFDSTPAGRILNRVSIDQSVVDLDIPFRL

GGFASTTIQLIGIVGVMTEVTWQVLLLVVPMAVACLWMQKYYMASSRELVRIVSTQKSPIIHLF

GESIAGASTIRGFGQEKRFMKRNLYLLDCFARPFFCSLSATEWLCLRMELLSTFVFAFCMVLLV

SFPRGSIDPSMAGLAVTYGLNLNARLSRWTLSFCKLENKIISIERIYQYSQIPSEAPTVIEDYR

PPSSWPENGTIEIIDLKIRYKENLPLVLYGVTCTFPGGKKIGIVGRTGSGKSTLIQALFRLIEP

TSGSILIDNINISEIGLHDLRSHLSIIPQDPTLFEGTIRGNLDPLDEHSDKEIWEALDKSQLGE

VIREKGQQLDTPVLENGDNWSVGQRQLVALGRALLQQSRILVLDEATASVDTATDNLIQKIIRS

EFKECTVCTIAHRiPTVTDSDLVLVLSDGRVAEFNTPSRLLEDKSSMFLKLVTEYSSRSSGiPD

F*

Glyma.02g01590_cDNA LEC1
SEQ ID NO: 5
ATGGCTACTTCAAAGTTGAAAACCCAGAATGTGGTTGTATCTCTCTCCCTAACCTTAACCTTGG

TACTGGTGCTACTGACCAGCAAGGCAAACTCAGCGGAAACTGTTTCTTTCAGCTGGAACAAGTT

CGTGCCGAAGCAACCAAACATGATCCTCCAAGGAGACGCTATTGTGACCTCCTCGGGAAAGTTA

CAACTCAATAAGGTTGACGAAAACGGCACCCCAAAACCCTCGTCTCTTGGTCGCGCCCTCTACT

CCACCCCCATCCACATTTGGGACAAAGAAACCGGTAGCGTTGCCAGCTTCGCCGCTTCCTTCAA

CTTCACCTTCTATGCCCCTGACACAAAAAGGCTTGCAGATGGGCTTGCCTTCTTTCTCGCACCA

ATTGACACTAAGCCACAAACACATGCAGGTTATCTTGGTCTTTTCAACGAAAACGAGTCTGGTG

ATCAAGTCGTCGCTGTTGAGTTTGACACTTTCCGGAACTCTTGGGATCCACCAAATCCACACAT

CGGAATTAACGTCAATTCTATCAGATCCATCAAAACGACGTCTTGGGATTTGGCCAACAATAAA

GTAGCCAAGGTTCTCATTACCTATGATGCCTCCACCAGCCTCTTGGTTGCTTCTTTGGTCTACC

CTTCACAGAGAACCAGCAATATCCTCTCCGATGTGGTCGATTTGAAGACTTCTCTTCCCGAGTG

GGTGAGGATAGGGTTCTCTGCTGCCACGGGACTCGACATACCTGGGGAATCGCATGACGTGCTT

TCTTGGTCTTTTGCTTCCAATTTGCCACACGCTAGCAGTAACATTGATCCTTTGGATCTTACAA

GCTTTGTGTTGCATGAGGCCATCTAA

Glyma.02g01590_PRT LEC1
SEQ ID NO: 6
MATSKLKTQNVVVSLSLTLTLVLVLLTSKANSAETVSFSWNKFVPKQPNMILQGDAIVTSSGKL

QLNKVDENGTPKPSSLGRALYSTPIHIWDKETGSVASFAASFNFTFYAPDTKRLADGLAFFLAP

IDTKPQTHAGYLGLFNENESGDQVVAVEFDTFRNSWDPPNPHIGINVNSIRSIKTTSWDLANNK

VAKVLITYDASTSLLVASLVYPSQRTSNILSDVVDLKTSLPEWVRIGFSAATGLDTIGESHDVL

SWSFASNLPHASSNIDPLDLTSFVLHEAT*

| | |
|---|---|
| Phytate-03g167800-F1<br>CCAGCAAACAACACAACAGAGCAGCAAAG | SEQ ID NO: 7 |
| Phytate-03g167800-R1<br>CTCCACGCATTTCCTCCAATTTCACTCTATATCTG | SEQ ID NO: 8 |
| Phytate-03g167800-F10<br>GGAAGGAGGCAGCTTGTAATGCCGTATTT | SEQ ID NO: 9 |
| Phytate-03g167800-R4<br>ACATGTTTCCTCATTGTATTTGTCTTGGCCTCTT | SEQ ID NO: 10 |
| Phytate-03g167800-F6<br>GGGAAAGAGCGGATACATTGCAAAGTGC | SEQ ID NO: 11 |
| Phytate-03g167800-R5<br>TGGATACCAAATTTAGCTCAGATGGAGGGTTATT | SEQ ID NO: 12 |
| Phytate-19g169000-F3<br>CTTCGTTGGCTTGGGCACTTCTCAAATC | SEQ ID NO: 13 |
| Phytate-19g169000-R4<br>AGAAACCTCACTTTGAAATACCGGAGGGC | SEQ ID NO: 14 |
| Lec02g_1_F1<br>GAGGATGGATTTAAACCAGTCAGCACCGTAAGT | SEQ ID NO: 15 |
| Lec02g_1_R1<br>GTTGCTGCTGTTCTTGTTTGCTCTGCGTTACT | SEQ ID NO: 16 |
| GXXXXGKS | SEQ ID NO: 17 |

---

What is claimed is:

1. A soybean plant comprising a non-transgenic mutation in an LPA-3 gene selected from the group consisting of: W328*, Q612*, and G1330D of SEQ ID NO. 2, and a non-transgenic mutation in an LPA-19 gene selected from the group consisting of: Q438* and G682S of SEQ ID NO. 4.

2. The soybean plant of claim 1, wherein said mutation in LPA-3 is Q612* of SEQ ID NO. 2 and said mutation in LPA-19 is G682S of SEQ ID NO. 4.

3. The soybean plant of claim 1, wherein said mutation in LPA-3 is G1330D of SEQ ID NO. 2 and said mutation in LPA-19 is Q438* of SEQ ID NO. 4.

4. The soybean plant of claim 1, wherein said mutation in LPA-3 is W328* of SEQ ID NO. 2 and said mutation in LPA-19 is G682S of SEQ ID NO. 4.

5. The soybean plant of claim 1, wherein said mutation in LPA-3 is W328* of SEQ ID NO. 2 and said mutation in LPA-19 is Q438* of SEQ ID NO. 4.

6. The soybean plant of claim 1, further comprising a non-transgenic mutation in the LEC-1 gene, wherein said mutation in LEC-1 is L228* of SEQ ID NO: 6.

7. A soybean plant of claim 1, wherein the phytate content of seeds of said plant is reduced by at least 80% compared to the phytate content of seeds of a non-mutagenized parent soybean plant.

8. Seed from a soybean plant of claim 1, wherein the seed comprises the non-transgenic mutations.

9. Soybean meal prepared from a soybean seed of claim 8.

10. A food product prepared using soybean meal of claim 9.

11. A food product prepared using the soybean seed of claim 8.

* * * * *

SEQUENCE LISTING

<160> NUMBER OF SEQ ID NOS: 17

<210> SEQ ID NO 1
<211> LENGTH: 4620
<212> TYPE: DNA
<213> ORGANISM: Glycine max

<400> SEQUENCE: 1

```
atggccgtcg atgaaattga atcttgtct cctacgtttt cttcttcggg atcgtttgag    60
acccttggaa gtgcgatcct cggattgcct ttgttggaac tggtggcaat ttgtgccaac   120
ttgacactgt ctcttctctt tctcttcgtt gtttcggcga ggaaggtgct tgtgtgtgta   180
gggagaggag taagatttgg taaggagaac ataaccggca atgccagccc cggttgtgtt   240
agtgttgatt tggaaacacg tgacgtcgtt cggattgaaa cgtggttcaa gttgtcggtg   300
ttgtcttgtt tgtatgttct gttggtgcaa gttttgctct ggggtttga tggggttgct   360
ttgattagag gaagggattt ggatgtggat ttggatttgg gtttggctct tctttctgtg   420
cctcttgtgc agggtttagc ttgggttgtg ttgagcttct cggctttgca atgcaagttc   480
aaggcgtctg agaggtttcc aattttgctc agacttggt gggttatgct gtttggtatt   540
tgtttgtgtg gtttgtatgt tgatggtaag ggggtttgga tggagggttc caagcacctg   600
cggtctcatg ttgtggcgaa tttccaccatc actcctgctc ttgcctttt gtgtattgtg   660
gcaattaggg gtgttactgg tataaaggtt tttaggaatt ccgaggagca ccagccattg   720
```

```
cttgttgagg aggaaccggg gtgtctcaag gttactcctt atactgatgc cggactttt      780
agcttggcca ctttgtcttg gttgaatcca cttctttcca taggggcaaa aaggccgctt     840
gagcttaagg acattcccct tgttgcggcg aaagaccgat ccaagacaaa ttataaggtt     900
ttgaattcta attgggagag gttgaaggct gaaaaccaat ccgagcagcc ttccttggct     960
tgggcacttc tcaagtcctt ctggaaggag gcagcttgta atgccgtatt tgctggtgtc    1020
actactcttg tctcgtatgt cggtccgtac atgataagtt actttgttga ttacttggtt    1080
ggcaaagaga ttttcccaca tgaggggtat gtccttgcag gggtattctt tgtggcaaag    1140
cttgtggaga cctttactac taggcagtgg tatcttgggg tggacatctt gggtatgcat    1200
gttaggtcgg ctctaactgc aatggtatat cgaaaggggc taaggatatc aagcttggcc    1260
aagcaaagtc acacgagtgg ggaggttgtt aactacatgg ctattgatgt tcagagggta    1320
ggggactact cttggtatct tcatgacatg tggatgcttc tctgcagat tgttcttgcc     1380
cttgcaattt tgtataagaa tgttggaatt gctgctattg caacactgat tgctacaata    1440
atttccatcg tcgtcactgt tcctattgcc agggtccaag aaaattatca agacaaatta    1500
atggctgcta aggatgaaag gatgagaaaa acatctgagt gcctgaggaa tatgaggatt    1560
ctcaaacttc aagcttggga ggacagatat agagtgaaat tggaggaaat gcgtggagta    1620
gagttcaagt ggcttcggaa agccctctat tctcaggctt tcataacttt catattctgg    1680
agctccccta tatttgtttc ggcggtcact tttgctactt ccatattgtt gggtggtcag    1740
ctgactgctg tggtgtact ttctgctctg gctactttca ggatcctgca agaacctttg     1800
aggaattttc cggacttggt gtcaacaatg gctcagacaa aggtttctct tgaccgatta    1860
tctggtttcc tgctggagga ggaattgcag gaagatgcaa ctattgtctt gccacaaggc    1920
attactaaca ttgctataga aattaaggat ggtatcttct gttgggaccc ttcttcatct    1980
tttaggccta cccatcagg gataagtatg aaagttgaaa gaaggatgcg cgtggctgtt     2040
tgtggtatgg ttggttcagg gaaatcgagt tttctttcgt gcatccttgg agagattcct    2100
aaactttctg gtgaagttag agtgtgtggc tcttctgctt atgtctccca atcagcgtgg    2160
atacaatcag gaactataga agaaaatatc ctctttggaa gcccaatgga caaagcaaag    2220
tacaagaatg ttcttcatgc ttgttcactg aaaaaggacc tagaactttt ctcacatggt    2280
gatcagacaa ttattgggga tagaggtata aacctgagtg gtggccagaa gcagcgggtt    2340
cagcttgcac gagcactcta ccaagatgct gatatttatc ttctggatga tcccttcagt    2400
gcagttgatg ctcacactgg atcagacttg tttaggggagt atatattgac agcacttgca    2460
gataaaacag tcatttttgt gacccatcaa gttgaatttc ttcccgctgc tgatttgatt    2520
ctggttctta aagaaggatg catcatacag tcaggaaagt atgatgatct tttacaagca    2580
ggaacagatt ttaatactct ggtttcagct caccatgaag ccatagaggc tatggatatc    2640
cctactcact cctctgaaga gtcagatgaa aatttatccc tggaggcatc tgttatgacc    2700
agtaagaaat ccatttgttc agcaaatgat atagacagtt tagcaaagga agtgcaagag    2760
ggatcatcta tttcagatca aaaagcaatt aaagagaaga agaagaaagc aaaacgatcg    2820
agaaagaaac agcttgttca ggaagaggag aggattagtg gtagagtcag catgaaggtg    2880
tatcttcat acatggcagc agcatataaa ggcttattga ttccactcat aatcattgca    2940
caaacattat ttcagttcct tcagattgca agcaattggt ggatggcttg gctaacccct    3000
caaacagaag gagacctgcc caaagtaact ccctcagttc ttcttcttgt ttatatggcc    3060
```

| | |
|---|---|
| cttgcttttg gcagctcatg gtttatattt gtaagggctg ttctggtggc tacatttggt | 3120 |
| cttgcagctg cccagaagct atttttgaaa atgcttagaa gtgttttcca tgcaccaatg | 3180 |
| tctttctttg actctacacc agctggaagg atcttgaatc gggtatcaat tgatcaaagt | 3240 |
| gttgtggatc ttgacattcc ttttagactt ggtggatttg cttcaactac aatacagctt | 3300 |
| attggtattg ttggtgtaat gacagaagtt acatggcaag ttttgctctt agttgtccca | 3360 |
| atggctgttg cttgtttgtg gatgcagaaa tactacatgg cttcctcaag ggaactggtt | 3420 |
| cgtattgtta gcatacagaa gtctccaatt atacatcttt ttggtgaatc aattgctgga | 3480 |
| gcatccacca tcaggggttt tggacaagaa aaaaggttca tgaagcggaa cctctatctt | 3540 |
| cttgattgct ttgcacgacc attcttctgc agtctttctg caattgagtg gctctgcctg | 3600 |
| cggatggagt tactgtcaac ctttgtattt gctttctgta tggtattact tgtgagtttt | 3660 |
| cctcgtggaa gtatcgaccc cagcatggct ggacttgctg tgacatatgg cctgaattta | 3720 |
| aatgcacgcc tatcacggtg atactcagc ttttgcaagc ttgaaaataa aattatatct | 3780 |
| attgagagaa tttatcagta cagccaaatt cctagtgaag cacccacaat tattgaagat | 3840 |
| tctcgccctc cattctcatg gccagaaaat gggacaattg aaataattga tttgaaggtc | 3900 |
| cgttacaagg agaatcttcc tatggtgctt catggagtaa catgcacatt tccaggtgga | 3960 |
| aagaagattg gaatagttgg acgtactggc agtggaaaat ctactttaat tcaggcgtta | 4020 |
| tttcgattga ttgaaccagc aagtgggagt atccttatag acaacattaa tatttcagag | 4080 |
| attggccttc atgaccttcg aagccatctc agtatcatac ctcaagatcc aaccttattt | 4140 |
| gaaggtacca ttcgaggcaa tcttgatcct ctggatgagc actcagataa agagatttgg | 4200 |
| gaggcacttg ataagtctca gcttggagag ttatccgtg agaaaggaca acagcttgac | 4260 |
| acaccagttc tagaaaatgg agataattgg agtgtaggac agcgacaact tgttgctctg | 4320 |
| ggccgagctc tgctgcagca gtcaagaata cttgtactgg atgaagcaac agcatcagtt | 4380 |
| gatactgcca cggataatct tatccagaag attatccgaa gtgagttcaa agactgcact | 4440 |
| gtttgcacca ttgcacatcg aataccact gtcattgaca gtgatctagt tcttgtgctc | 4500 |
| agtgatggtc tagtcgcaga gttcgacact ccttcaagac tattagagga taagtcatcc | 4560 |
| gtgtttctga agttggtgac cgagtattca tcacgttcaa gtggcatacc agactttag | 4620 |

<210> SEQ ID NO 2
<211> LENGTH: 1539
<212> TYPE: PRT
<213> ORGANISM: Glycine max

<400> SEQUENCE: 2

```
Met Ala Val Asp Glu Ile Glu Ile Leu Ser Pro Thr Phe Ser Ser
1               5                   10                  15

Gly Ser Phe Glu Thr Leu Trp Ser Ala Ile Leu Gly Leu Pro Leu Leu
            20                  25                  30

Glu Leu Val Ala Ile Cys Ala Asn Leu Thr Leu Ser Leu Leu Phe Leu
        35                  40                  45

Phe Val Val Ser Ala Arg Lys Val Leu Val Cys Val Gly Arg Gly Val
    50                  55                  60

Arg Phe Gly Lys Glu Asn Ile Thr Gly Asn Ala Ser Pro Gly Cys Val
65                  70                  75                  80

Ser Val Asp Leu Glu Thr Arg Asp Val Arg Ile Glu Thr Trp Phe
                85                  90                  95

Lys Leu Ser Val Leu Ser Cys Leu Tyr Val Leu Leu Val Gln Val Leu
```

-continued

```
                100             105                 110
Leu Leu Gly Phe Asp Gly Val Ala Leu Ile Arg Gly Arg Asp Leu Asp
        115                 120                 125

Val Asp Leu Asp Leu Gly Leu Ala Leu Leu Ser Val Pro Leu Val Gln
130                 135                 140

Gly Leu Ala Trp Val Val Leu Ser Phe Ser Ala Leu Gln Cys Lys Phe
145                 150                 155                 160

Lys Ala Ser Glu Arg Phe Pro Ile Leu Arg Leu Trp Trp Val Met
                165                 170                 175

Leu Phe Gly Ile Cys Leu Cys Gly Leu Tyr Val Asp Gly Lys Gly Val
            180                 185                 190

Trp Met Glu Gly Ser Lys His Leu Arg Ser His Val Ala Asn Phe
        195                 200                 205

Thr Ile Thr Pro Ala Leu Ala Phe Leu Cys Ile Val Ala Ile Arg Gly
        210                 215                 220

Val Thr Gly Ile Lys Val Phe Arg Asn Ser Glu Glu His Gln Pro Leu
225                 230                 235                 240

Leu Val Glu Glu Glu Pro Gly Cys Leu Lys Val Thr Pro Tyr Thr Asp
                245                 250                 255

Ala Gly Leu Phe Ser Leu Ala Thr Leu Ser Trp Leu Asn Pro Leu Leu
            260                 265                 270

Ser Ile Gly Ala Lys Arg Pro Leu Glu Leu Lys Asp Ile Pro Leu Val
            275                 280                 285

Ala Ala Lys Asp Arg Ser Lys Thr Asn Tyr Lys Val Leu Asn Ser Asn
        290                 295                 300

Trp Glu Arg Leu Lys Ala Glu Asn Gln Ser Glu Gln Pro Ser Leu Ala
305                 310                 315                 320

Trp Ala Leu Leu Lys Ser Phe Trp Lys Glu Ala Cys Asn Ala Val
                325                 330                 335

Phe Ala Gly Val Thr Thr Leu Val Ser Tyr Val Gly Pro Tyr Met Ile
            340                 345                 350

Ser Tyr Phe Val Asp Tyr Leu Val Gly Lys Glu Ile Phe Pro His Glu
        355                 360                 365

Gly Tyr Val Leu Ala Gly Val Phe Phe Val Ala Lys Leu Val Glu Thr
        370                 375                 380

Phe Thr Thr Arg Gln Trp Tyr Leu Gly Val Asp Ile Leu Gly Met His
385                 390                 395                 400

Val Arg Ser Ala Leu Thr Ala Met Val Tyr Arg Lys Gly Leu Arg Ile
                405                 410                 415

Ser Ser Leu Ala Lys Gln Ser His Thr Ser Gly Glu Val Val Asn Tyr
            420                 425                 430

Met Ala Ile Asp Val Gln Arg Val Gly Asp Tyr Ser Trp Tyr Leu His
            435                 440                 445

Asp Met Trp Met Leu Pro Leu Gln Ile Val Leu Ala Leu Ala Ile Leu
        450                 455                 460

Tyr Lys Asn Val Gly Ile Ala Ala Ile Ala Thr Leu Ile Ala Thr Ile
465                 470                 475                 480

Ile Ser Ile Val Val Thr Val Pro Ile Ala Arg Val Gln Glu Asn Tyr
                485                 490                 495

Gln Asp Lys Leu Met Ala Ala Lys Asp Glu Arg Met Arg Lys Thr Ser
            500                 505                 510

Glu Cys Leu Arg Asn Met Arg Ile Leu Lys Leu Gln Ala Trp Glu Asp
        515                 520                 525
```

```
Arg Tyr Arg Val Lys Leu Glu Glu Met Arg Gly Val Glu Phe Lys Trp
        530                 535                 540

Leu Arg Lys Ala Leu Tyr Ser Gln Ala Phe Ile Thr Phe Ile Phe Trp
545                 550                 555                 560

Ser Ser Pro Ile Phe Val Ser Ala Val Thr Phe Ala Thr Ser Ile Leu
                565                 570                 575

Leu Gly Gly Gln Leu Thr Ala Gly Gly Val Leu Ser Ala Leu Ala Thr
            580                 585                 590

Phe Arg Ile Leu Gln Glu Pro Leu Arg Asn Phe Pro Asp Leu Val Ser
        595                 600                 605

Thr Met Ala Gln Thr Lys Val Ser Leu Asp Arg Leu Ser Gly Phe Leu
610                 615                 620

Leu Glu Glu Glu Leu Gln Glu Asp Ala Thr Ile Val Leu Pro Gln Gly
625                 630                 635                 640

Ile Thr Asn Ile Ala Ile Glu Ile Lys Asp Gly Ile Phe Cys Trp Asp
                645                 650                 655

Pro Ser Ser Ser Phe Arg Pro Thr Leu Ser Gly Ile Ser Met Lys Val
            660                 665                 670

Glu Arg Arg Met Arg Val Ala Val Cys Gly Met Val Gly Ser Gly Lys
        675                 680                 685

Ser Ser Phe Leu Ser Cys Ile Leu Gly Glu Ile Pro Lys Leu Ser Gly
690                 695                 700

Glu Val Arg Val Cys Gly Ser Ser Ala Tyr Val Ser Gln Ser Ala Trp
705                 710                 715                 720

Ile Gln Ser Gly Thr Ile Glu Glu Asn Ile Leu Phe Gly Ser Pro Met
                725                 730                 735

Asp Lys Ala Lys Tyr Lys Asn Val Leu His Ala Cys Ser Leu Lys Lys
            740                 745                 750

Asp Leu Glu Leu Phe Ser His Gly Asp Gln Thr Ile Ile Gly Asp Arg
        755                 760                 765

Gly Ile Asn Leu Ser Gly Gly Gln Lys Gln Arg Val Gln Leu Ala Arg
770                 775                 780

Ala Leu Tyr Gln Asp Ala Asp Ile Tyr Leu Leu Asp Asp Pro Phe Ser
785                 790                 795                 800

Ala Val Asp Ala His Thr Gly Ser Asp Leu Phe Arg Glu Tyr Ile Leu
                805                 810                 815

Thr Ala Leu Ala Asp Lys Thr Val Ile Phe Val Thr His Gln Val Glu
            820                 825                 830

Phe Leu Pro Ala Ala Asp Leu Ile Leu Val Leu Lys Glu Gly Cys Ile
        835                 840                 845

Ile Gln Ser Gly Lys Tyr Asp Asp Leu Leu Gln Ala Gly Thr Asp Phe
850                 855                 860

Asn Thr Leu Val Ser Ala His His Glu Ala Ile Glu Ala Met Asp Ile
865                 870                 875                 880

Pro Thr His Ser Ser Glu Glu Ser Asp Glu Asn Leu Ser Leu Glu Ala
                885                 890                 895

Ser Val Met Thr Ser Lys Lys Ser Ile Cys Ser Ala Asn Asp Ile Asp
            900                 905                 910

Ser Leu Ala Lys Glu Val Gln Glu Gly Ser Ser Ile Ser Asp Gln Lys
        915                 920                 925

Ala Ile Lys Glu Lys Lys Lys Ala Lys Arg Ser Arg Lys Lys Gln
930                 935                 940
```

```
Leu Val Gln Glu Glu Glu Arg Ile Arg Gly Arg Val Ser Met Lys Val
945                 950                 955                 960

Tyr Leu Ser Tyr Met Ala Ala Ala Tyr Lys Gly Leu Leu Ile Pro Leu
            965                 970                 975

Ile Ile Ile Ala Gln Thr Leu Phe Gln Phe Leu Gln Ile Ala Ser Asn
                980                 985                 990

Trp Trp Met Ala Trp Ala Asn Pro Gln Thr Glu Gly Asp Leu Pro Lys
            995                 1000                1005

Val Thr Pro Ser Val Leu Leu Val Tyr Met Ala Leu Ala Phe
1010                1015                1020

Gly Ser Ser Trp Phe Ile Phe Val Arg Ala Val Leu Val Ala Thr
1025                1030                1035

Phe Gly Leu Ala Ala Ala Gln Lys Leu Phe Leu Lys Met Leu Arg
1040                1045                1050

Ser Val Phe His Ala Pro Met Ser Phe Asp Ser Thr Pro Ala
1055                1060                1065

Gly Arg Ile Leu Asn Arg Val Ser Ile Asp Gln Ser Val Val Asp
1070                1075                1080

Leu Asp Ile Pro Phe Arg Leu Gly Gly Phe Ala Ser Thr Thr Ile
1085                1090                1095

Gln Leu Ile Gly Ile Val Gly Val Met Thr Glu Val Thr Trp Gln
1100                1105                1110

Val Leu Leu Val Val Pro Met Ala Val Ala Cys Leu Trp Met
1115                1120                1125

Gln Lys Tyr Tyr Met Ala Ser Ser Arg Glu Leu Val Arg Ile Val
1130                1135                1140

Ser Ile Gln Lys Ser Pro Ile Ile His Leu Phe Gly Glu Ser Ile
1145                1150                1155

Ala Gly Ala Ser Thr Ile Arg Gly Phe Gly Gln Glu Lys Arg Phe
1160                1165                1170

Met Lys Arg Asn Leu Tyr Leu Leu Asp Cys Phe Ala Arg Pro Phe
1175                1180                1185

Phe Cys Ser Leu Ser Ala Ile Glu Trp Leu Cys Leu Arg Met Glu
1190                1195                1200

Leu Leu Ser Thr Phe Val Phe Ala Phe Cys Met Val Leu Leu Val
1205                1210                1215

Ser Phe Pro Arg Gly Ser Ile Asp Pro Ser Met Ala Gly Leu Ala
1220                1225                1230

Val Thr Tyr Gly Leu Asn Leu Asn Ala Arg Leu Ser Arg Trp Ile
1235                1240                1245

Leu Ser Phe Cys Lys Leu Glu Asn Lys Ile Ile Ser Ile Glu Arg
1250                1255                1260

Ile Tyr Gln Tyr Ser Gln Ile Pro Ser Glu Ala Pro Thr Ile Ile
1265                1270                1275

Glu Asp Ser Arg Pro Pro Phe Ser Trp Pro Glu Asn Gly Thr Ile
1280                1285                1290

Glu Ile Ile Asp Leu Lys Val Arg Tyr Lys Glu Asn Leu Pro Met
1295                1300                1305

Val Leu His Gly Val Thr Cys Thr Phe Pro Gly Gly Lys Lys Ile
1310                1315                1320

Gly Ile Val Gly Arg Thr Gly Ser Gly Lys Ser Thr Leu Ile Gln
1325                1330                1335

Ala Leu Phe Arg Leu Ile Glu Pro Ala Ser Gly Ser Ile Leu Ile
```

Asp Asn Ile Asn Ile Ser Glu Ile Gly Leu His Asp Leu Arg Ser
1355                1360                1365

His Leu Ser Ile Ile Pro Gln Asp Pro Thr Leu Phe Glu Gly Thr
1370                1375                1380

Ile Arg Gly Asn Leu Asp Pro Leu Asp Glu His Ser Asp Lys Glu
1385                1390                1395

Ile Trp Glu Ala Leu Asp Lys Ser Gln Leu Gly Glu Val Ile Arg
1400                1405                1410

Glu Lys Gly Gln Gln Leu Asp Thr Pro Val Leu Glu Asn Gly Asp
1415                1420                1425

Asn Trp Ser Val Gly Gln Arg Gln Leu Val Ala Leu Gly Arg Ala
1430                1435                1440

Leu Leu Gln Gln Ser Arg Ile Leu Val Leu Asp Glu Ala Thr Ala
1445                1450                1455

Ser Val Asp Thr Ala Thr Asp Asn Leu Ile Gln Lys Ile Ile Arg
1460                1465                1470

Ser Glu Phe Lys Asp Cys Thr Val Cys Thr Ile Ala His Arg Ile
1475                1480                1485

Pro Thr Val Ile Asp Ser Asp Leu Val Leu Val Leu Ser Asp Gly
1490                1495                1500

Leu Val Ala Glu Phe Asp Thr Pro Ser Arg Leu Leu Glu Asp Lys
1505                1510                1515

Ser Ser Val Phe Leu Lys Leu Val Thr Glu Tyr Ser Ser Arg Ser
1520                1525                1530

Ser Gly Ile Pro Asp Phe
1535

<210> SEQ ID NO 3
<211> LENGTH: 4614
<212> TYPE: DNA
<213> ORGANISM: Glycine max

<400> SEQUENCE: 3

```
atggccgtcg atgaaattga atattgtct  tcgacgttgt tttcttcttc ttcttcggga    60
tcgttttgaga tcctttggag tgcgatcctc ggattgcctt tgttggaact ggtggcaatc   120
tgtgccaacc tgcactgtt  tattctcttt ctcgtcgttg tttcggcgag aaggtgctt    180
gtgtgtgtat ggggaggagt tagattcggt aaggagaacg gaaccggcaa tgccagcccc   240
ggttgtgtta tgtgttgattt ggaaacacgt gacattcgga ttgaaacgtg ttcaagttg   300
tcggtgttgt cttgtttcta tgttctgttg gtgcaagttt tggtcttggg gtttgatggg   360
gttgctttga ttagaggaag ggatttggat ttggatttgg gtttggctct tctttctgtg   420
cctcttgtgc agggtttagc ttgggttgtg ttgagcttct cggctttgca atgcaaattc   480
aaggcgtgtg agaggtttcc agttttgctt agagtttggt tatttgtggt gttcgttatt   540
tgtttgtgtg gtttgtatgt tgatggaagg ggggtttgga tggaaggttc caagcacctg   600
cgttctcatg ttgtggcgaa tttcgccgtc actcctgctc ttgcctttt  gtgtattgtg   660
gcaattaggg gtgttactgg tataaaggtt tttaggagtt ctgaggagca acagccattg   720
cttgttgatg aggatcccgg gtgtctcaag gttactcctt atagtgatgc tggactttt    780
agcttggcca ttttgtcttg gttgaatcca cttctttcca ttggggcaaa aaggccgctt   840
gagcttaagg acattcccct tgttgcgccg aaagaccgat ccaagacaaa ttataaggtt   900
```

```
ttgaattcta attgggagag gttgaaggct gaaaacctat ccgggcagcc ttcgttggct    960
tgggcacttc tcaaatcctt ctggaaggag gcggcttgta acgctgtgtt tgctggtgtc   1020
actactcttg tctcgtatgt tggtccatat atgataagtt actttgttga ttacttggtt   1080
ggcaaagaga ttttcccaca tgaggggtat gtccttgcag gggtattctt tgtggcaaag   1140
cttgtggaga cctttactac taggcagtgg tatcttgggg tggatatctt gggtatgcat   1200
gttaggtcgg ctctaactgc aatggtatat cgaaaggggc taaggatatc aagcttggcc   1260
aagcaaagtc acacgagcgg ggaggttgtt aactacatgg ctattgatgt tcagagggta   1320
ggggactact cttggtatct tcatgacatg tggatgcttc ctctgcagat tgttcttgcc   1380
cttgcgattt tgtataagaa tgttggaatt gcttctattg caacactgat tgctacaata   1440
atttccatcg cggtcactgt tcctattgcc aggatccaag aaaattatca agacaaatta   1500
atggctgcta aggatgaaag gatgagaaaa acatctgagt gcctgaggaa tatgaggatt   1560
ctcaaacttc aagcttggga ggatagatat agagtgaaat tggaggaaat gcgaggagta   1620
gagttcaagt ggcttcggaa agctctctat tctcaggctt tcataacttt catattctgg   1680
agctccccta tatttgtttc agcagtcact tttggtactt ccatattgtt gggtggtcag   1740
ctgactgctg gtggtgtact ttctgctttg gctactttca ggatcctgca agaaccttg    1800
aggaattttc cggacttggt gtcaacaatg gctcagacaa aggtttctct tgaccgatta   1860
tctggtttcc tgctggagga ggaattgcag gaagatgcaa ctattgtctt gccacaaggc   1920
attactaaca ttgctataga aattaagggt ggtgtcttct gttgggaccc ttcttcatct   1980
tctagaccta cccatcagg gataagtatg aagttgaaa gaaggatgcg tgtggctgtt    2040
tgtggtatgg ttggttcagg gaaatcaagt tttcttttgt gcatccttgg agagattcct   2100
aaaatttctg gtgaagttag agtgtgtggc tcttctgcat atgtctccca atcagcatgg   2160
atacaatcag gaactataga agaaaatatc ctctttggaa gcccaatgga caaagcaaag   2220
tacaagaatg ttcttcatgc ttgttcactg aaaaaggacc tagaactttt ctcacatggt   2280
gatcttacaa ttattgggga tagaggtata aacctgagtg gtggccagaa gcagcgggtt   2340
cagctggctc gggcactcta ccaagatgct gatatttatc ttcttgatga tcccttcagt   2400
gcagttgatg ctcacactgg atcagacttg tttagggagt atatattgac agcacttgca   2460
gataaaacag tcatttatgt gacccatcaa gttgaatttc ttcctgctgc tgatttgata   2520
ttggttctca agaaggatg catcatacag tcaggaaagt atgacgatct tttacaagca   2580
ggaacagatt ttaatactct ggtttcagct cacaatgaag ccatagaggc catggatatc   2640
cctactcact ctgaagattc agatgaaaat ttatccctgg aggcatgtgt tatgaccagt   2700
aagaaatcca tttgttctgc aaatgatata gacagtttgg caaggaagt gcaagaggga   2760
tcatctattt cagatcaaaa agcaattaaa gagaagaaga agcaaaacg atcgagaaag   2820
aaacagcttg ttcaggaaga gggagaggatt agaggtagag tcagcatgaa ggtgtatttg   2880
tcatacatgg cagcagcata taaggcttta ttgattccac tcataatcat tgcacaaaca   2940
ttatttcagt tccttcagat tgctagcaat tggtggatgg cttgggctaa tcctcaaaca   3000
gaaggagacc tgcccaaagt aactccctca gttcttcttc ttgtttatat ggcccttgct   3060
tttggcagct catggttta atttgtaagg gctgttctgg tggctacgtt tggtcttgca   3120
gctgcacaga agctattttt gaaaatgctt agaagtgttt tccatgcacc aatgtctttc   3180
tttgactcta caccagctgg aaggattttg aatcgggtat caattgatca agtgttgtg    3240
gatcttgaca ttccttttag acttggtggg tttgcttcaa caacaataca gcttattggt   3300
```

-continued

```
attgttggtg taatgacaga agttacgtgg caagttttgc tcttagttgt cccaatggct  3360
gttgcttgtt tgtggatgca gaaatactac atggcttcct caagggaact ggttcgaatt  3420
gttagcatcc agaagtctcc aattatacat cttttggtg aatctattgc tggagcatcc   3480
accatcaggg gttttggaca agaaaaaagg ttcatgaagc gaaacctcta tcttcttgat  3540
tgctttgcac gaccattctt ctgcagtctt tctgcaattg agtggctctg cctgcggatg  3600
gagttactgt caacctttgt atttgctttc tgtatggtat tacttgtgag ttttcctcgt  3660
ggaagtatcg accccagcat ggctggactt gctgtgacat atggcctgaa tttaaatgca  3720
cgtctatcac ggtggatact cagcttttgc aaacttgaaa ataaaattat atctattgag  3780
agaatttatc agtacagcca aattcctagt gaagcaccca cagttattga agattatcgc  3840
cctccatcct catggcctga aaatgggaca attgaaataa ttgatttgaa gattcgttac  3900
aaggagaatc ttcctttggt gctttatgga gtaacatgca catttcctgg tggaaagaag  3960
attggaatag taggacgtac tggcagtgga aaatctactt taattcaggc gttatttcga  4020
ttgattgaac caacaagtgg gagtatcctt atagacaaca ttaatatttc agagattggc  4080
cttcatgacc ttcgaagcca tctcagtatc ataccacaag atccaacctt atttgaaggt  4140
accattcgag gcaatcttga tcctctggat gagcactcag ataaagagat tgggaggca   4200 cttgataagt ctcagcttgg agaggttatc cgtgagaaag gacaacagct tgatacgcca  4260
gttctagaaa atggagataa ttggagtgta ggacagcgac aacttgttgc tctgggccga  4320
gctctgctgc agcagtcaag aatacttgta ctagatgaag caacagcatc agttgatacc  4380
gccacagata atcttataca gaagattatc cgaagtgagt tcaaagaatg cactgtttgc  4440
accattgcac atcgaatacc tactgtcatt gacagtgatc tagttcttgt gctcagtgat  4500
ggtcgagttg cagagttcaa cactccttca agactattag aggataagtc atccatgttt  4560
ctgaagctgg tgactgagta ctcatcacgt tcaagtggca taccagactt ttag         4614
```

<210> SEQ ID NO 4
<211> LENGTH: 1537
<212> TYPE: PRT
<213> ORGANISM: Glycine max

<400> SEQUENCE: 4

```
Met Ala Val Asp Glu Ile Glu Ile Leu Ser Ser Thr Leu Phe Ser Ser
1               5                   10                  15

Ser Ser Ser Gly Ser Phe Glu Ile Leu Trp Ser Ala Ile Leu Gly Leu
            20                  25                  30

Pro Leu Leu Glu Leu Val Ala Ile Cys Ala Asn Leu Thr Leu Phe Ile
        35                  40                  45

Leu Phe Leu Val Val Val Ser Ala Arg Lys Val Leu Val Cys Val Trp
    50                  55                  60

Gly Gly Val Arg Phe Gly Lys Glu Asn Gly Thr Gly Asn Ala Ser Pro
65                  70                  75                  80

Gly Cys Val Ser Val Asp Leu Glu Thr Arg Asp Ile Arg Ile Glu Thr
                85                  90                  95

Trp Phe Lys Leu Ser Val Leu Ser Cys Phe Tyr Val Leu Leu Val Gln
            100                 105                 110

Val Leu Val Leu Gly Phe Asp Gly Val Ala Leu Ile Arg Gly Arg Asp
        115                 120                 125

Leu Asp Leu Asp Leu Gly Leu Ala Leu Leu Ser Val Pro Leu Val Gln
    130                 135                 140
```

```
Gly Leu Ala Trp Val Val Leu Ser Phe Ser Ala Leu Gln Cys Lys Phe
145                 150                 155                 160

Lys Ala Cys Glu Arg Phe Pro Val Leu Leu Arg Val Trp Leu Phe Val
            165                 170                 175

Val Phe Val Ile Cys Leu Cys Gly Leu Tyr Val Asp Gly Arg Gly Val
            180                 185                 190

Trp Met Glu Gly Ser Lys His Leu Arg Ser His Val Val Ala Asn Phe
            195                 200                 205

Ala Val Thr Pro Ala Leu Ala Phe Leu Cys Ile Val Ala Ile Arg Gly
            210                 215                 220

Val Thr Gly Ile Lys Val Phe Arg Ser Ser Glu Glu Gln Pro Leu
225                 230                 235                 240

Leu Val Asp Glu Asp Pro Gly Cys Leu Lys Val Thr Pro Tyr Ser Asp
            245                 250                 255

Ala Gly Leu Phe Ser Leu Ala Ile Leu Ser Trp Leu Asn Pro Leu Leu
            260                 265                 270

Ser Ile Gly Ala Lys Arg Pro Leu Glu Leu Lys Asp Ile Pro Leu Val
            275                 280                 285

Ala Pro Lys Asp Arg Ser Lys Thr Asn Tyr Lys Val Leu Asn Ser Asn
290                 295                 300

Trp Glu Arg Leu Lys Ala Glu Asn Leu Ser Gly Gln Pro Ser Leu Ala
305                 310                 315                 320

Trp Ala Leu Leu Lys Ser Phe Trp Lys Glu Ala Ala Cys Asn Ala Val
            325                 330                 335

Phe Ala Gly Val Thr Thr Leu Val Ser Tyr Val Gly Pro Tyr Met Ile
            340                 345                 350

Ser Tyr Phe Val Asp Tyr Leu Val Gly Lys Glu Ile Phe Pro His Glu
            355                 360                 365

Gly Tyr Val Leu Ala Gly Val Phe Phe Val Ala Lys Leu Val Glu Thr
            370                 375                 380

Phe Thr Thr Arg Gln Trp Tyr Leu Gly Val Asp Ile Leu Gly Met His
385                 390                 395                 400

Val Arg Ser Ala Leu Thr Ala Met Val Tyr Arg Lys Gly Leu Arg Ile
            405                 410                 415

Ser Ser Leu Ala Lys Gln Ser His Thr Ser Gly Glu Val Val Asn Tyr
            420                 425                 430

Met Ala Ile Asp Val Gln Arg Val Gly Asp Tyr Ser Trp Tyr Leu His
            435                 440                 445

Asp Met Trp Met Leu Pro Leu Gln Ile Val Leu Ala Leu Ala Ile Leu
            450                 455                 460

Tyr Lys Asn Val Gly Ile Ala Ser Ile Ala Thr Leu Ile Ala Thr Ile
465                 470                 475                 480

Ile Ser Ile Ala Val Thr Val Pro Ile Ala Arg Ile Gln Glu Asn Tyr
            485                 490                 495

Gln Asp Lys Leu Met Ala Ala Lys Asp Glu Arg Met Arg Lys Thr Ser
            500                 505                 510

Glu Cys Leu Arg Asn Met Arg Ile Leu Lys Leu Gln Ala Trp Glu Asp
            515                 520                 525

Arg Tyr Arg Val Lys Leu Glu Glu Met Arg Gly Val Glu Phe Lys Trp
            530                 535                 540

Leu Arg Lys Ala Leu Tyr Ser Gln Ala Phe Ile Thr Phe Ile Phe Trp
545                 550                 555                 560
```

```
Ser Ser Pro Ile Phe Val Ser Ala Val Thr Phe Gly Thr Ser Ile Leu
                565                 570                 575

Leu Gly Gly Gln Leu Thr Ala Gly Gly Val Leu Ser Ala Leu Ala Thr
            580                 585                 590

Phe Arg Ile Leu Gln Glu Pro Leu Arg Asn Phe Pro Asp Leu Val Ser
        595                 600                 605

Thr Met Ala Gln Thr Lys Val Ser Leu Asp Arg Leu Ser Gly Phe Leu
    610                 615                 620

Leu Glu Glu Glu Leu Gln Glu Asp Ala Thr Ile Val Leu Pro Gln Gly
625                 630                 635                 640

Ile Thr Asn Ile Ala Ile Glu Ile Lys Gly Gly Val Phe Cys Trp Asp
                645                 650                 655

Pro Ser Ser Ser Arg Pro Thr Leu Ser Gly Ile Ser Met Lys Val
            660                 665                 670

Glu Arg Arg Met Arg Val Ala Val Cys Gly Met Val Gly Ser Gly Lys
        675                 680                 685

Ser Ser Phe Leu Leu Cys Ile Leu Gly Glu Ile Pro Lys Ile Ser Gly
    690                 695                 700

Glu Val Arg Val Cys Gly Ser Ser Ala Tyr Val Ser Gln Ser Ala Trp
705                 710                 715                 720

Ile Gln Ser Gly Thr Ile Glu Glu Asn Ile Leu Phe Gly Ser Pro Met
                725                 730                 735

Asp Lys Ala Lys Tyr Lys Asn Val Leu His Ala Cys Ser Leu Lys Lys
            740                 745                 750

Asp Leu Glu Leu Phe Ser His Gly Asp Leu Thr Ile Ile Gly Asp Arg
        755                 760                 765

Gly Ile Asn Leu Ser Gly Gly Gln Lys Gln Arg Val Gln Leu Ala Arg
    770                 775                 780

Ala Leu Tyr Gln Asp Ala Asp Ile Tyr Leu Leu Asp Asp Pro Phe Ser
785                 790                 795                 800

Ala Val Asp Ala His Thr Gly Ser Asp Leu Phe Arg Glu Tyr Ile Leu
                805                 810                 815

Thr Ala Leu Ala Asp Lys Thr Val Ile Tyr Val Thr His Gln Val Glu
            820                 825                 830

Phe Leu Pro Ala Ala Asp Leu Ile Leu Val Leu Lys Glu Gly Cys Ile
        835                 840                 845

Ile Gln Ser Gly Lys Tyr Asp Asp Leu Leu Gln Ala Gly Thr Asp Phe
    850                 855                 860

Asn Thr Leu Val Ser Ala His Asn Glu Ala Ile Glu Ala Met Asp Ile
865                 870                 875                 880

Pro Thr His Ser Glu Asp Ser Asp Glu Asn Leu Ser Leu Glu Ala Cys
                885                 890                 895

Val Met Thr Ser Lys Lys Ser Ile Cys Ser Ala Asn Asp Ile Asp Ser
            900                 905                 910

Leu Ala Lys Glu Val Gln Glu Gly Ser Ser Ile Ser Asp Gln Lys Ala
        915                 920                 925

Ile Lys Glu Lys Lys Lys Ala Lys Arg Ser Arg Lys Lys Gln Leu Val
    930                 935                 940

Gln Glu Glu Glu Arg Ile Arg Gly Arg Val Ser Met Lys Val Tyr Leu
945                 950                 955                 960

Ser Tyr Met Ala Ala Ala Tyr Lys Gly Leu Leu Ile Pro Leu Ile Ile
                965                 970                 975

Ile Ala Gln Thr Leu Phe Gln Phe Leu Gln Ile Ala Ser Asn Trp Trp
```

```
            980             985             990
Met Ala Trp Ala Asn Pro Gln Thr Glu Gly Asp Leu Pro Lys Val Thr
                995            1000           1005

Pro Ser Val Leu Leu Leu Val Tyr Met Ala Leu Ala Phe Gly Ser
   1010           1015           1020

Ser Trp Phe Ile Phe Val Arg Ala Val Leu Val Ala Thr Phe Gly
   1025           1030           1035

Leu Ala Ala Ala Gln Lys Leu Phe Leu Lys Met Leu Arg Ser Val
   1040           1045           1050

Phe His Ala Pro Met Ser Phe Asp Ser Thr Pro Ala Gly Arg
   1055           1060           1065

Ile Leu Asn Arg Val Ser Ile Asp Gln Ser Val Val Asp Leu Asp
   1070           1075           1080

Ile Pro Phe Arg Leu Gly Gly Phe Ala Ser Thr Thr Ile Gln Leu
   1085           1090           1095

Ile Gly Ile Val Gly Val Met Thr Glu Val Thr Trp Gln Val Leu
   1100           1105           1110

Leu Leu Val Val Pro Met Ala Val Ala Cys Leu Trp Met Gln Lys
   1115           1120           1125

Tyr Tyr Met Ala Ser Ser Arg Glu Leu Val Arg Ile Val Ser Ile
   1130           1135           1140

Gln Lys Ser Pro Ile Ile His Leu Phe Gly Glu Ser Ile Ala Gly
   1145           1150           1155

Ala Ser Thr Ile Arg Gly Phe Gly Gln Glu Lys Arg Phe Met Lys
   1160           1165           1170

Arg Asn Leu Tyr Leu Leu Asp Cys Phe Ala Arg Pro Phe Phe Cys
   1175           1180           1185

Ser Leu Ser Ala Ile Glu Trp Leu Cys Leu Arg Met Glu Leu Leu
   1190           1195           1200

Ser Thr Phe Val Phe Ala Phe Cys Met Val Leu Leu Val Ser Phe
   1205           1210           1215

Pro Arg Gly Ser Ile Asp Pro Ser Met Ala Gly Leu Ala Val Thr
   1220           1225           1230

Tyr Gly Leu Asn Leu Asn Ala Arg Leu Ser Arg Trp Ile Leu Ser
   1235           1240           1245

Phe Cys Lys Leu Glu Asn Lys Ile Ile Ser Ile Glu Arg Ile Tyr
   1250           1255           1260

Gln Tyr Ser Gln Ile Pro Ser Glu Ala Pro Thr Val Ile Glu Asp
   1265           1270           1275

Tyr Arg Pro Pro Ser Ser Trp Pro Glu Asn Gly Thr Ile Glu Ile
   1280           1285           1290

Ile Asp Leu Lys Ile Arg Tyr Lys Glu Asn Leu Pro Leu Val Leu
   1295           1300           1305

Tyr Gly Val Thr Cys Thr Phe Pro Gly Gly Lys Lys Ile Gly Ile
   1310           1315           1320

Val Gly Arg Thr Gly Ser Gly Lys Ser Thr Leu Ile Gln Ala Leu
   1325           1330           1335

Phe Arg Leu Ile Glu Pro Thr Ser Gly Ser Ile Leu Ile Asp Asn
   1340           1345           1350

Ile Asn Ile Ser Glu Ile Gly Leu His Asp Leu Arg Ser His Leu
   1355           1360           1365

Ser Ile Ile Pro Gln Asp Pro Thr Leu Phe Glu Gly Thr Ile Arg
   1370           1375           1380
```

```
Gly Asn Leu Asp Pro Leu Asp Glu His Ser Asp Lys Glu Ile Trp
    1385               1390                1395
Glu Ala Leu Asp Lys Ser Gln Leu Gly Glu Val Ile Arg Glu Lys
    1400               1405                1410
Gly Gln Gln Leu Asp Thr Pro Val Leu Glu Asn Gly Asp Asn Trp
    1415               1420                1425
Ser Val Gly Gln Arg Gln Leu Val Ala Leu Gly Arg Ala Leu Leu
    1430               1435                1440
Gln Gln Ser Arg Ile Leu Val Leu Asp Glu Ala Thr Ala Ser Val
    1445               1450                1455
Asp Thr Ala Thr Asp Asn Leu Ile Gln Lys Ile Ile Arg Ser Glu
    1460               1465                1470
Phe Lys Glu Cys Thr Val Cys Thr Ile Ala His Arg Ile Pro Thr
    1475               1480                1485
Val Ile Asp Ser Asp Leu Val Leu Val Leu Ser Asp Gly Arg Val
    1490               1495                1500
Ala Glu Phe Asn Thr Pro Ser Arg Leu Leu Glu Asp Lys Ser Ser
    1505               1510                1515
Met Phe Leu Lys Leu Val Thr Glu Tyr Ser Ser Arg Ser Ser Gly
    1520               1525                1530
Ile Pro Asp Phe
    1535
```

<210> SEQ ID NO 5
<211> LENGTH: 858
<212> TYPE: DNA
<213> ORGANISM: Glycine max

<400> SEQUENCE: 5

```
atggctactt caaagttgaa aacccagaat gtggttgtat ctctctccct aaccttaacc      60
ttggtactgg tgctactgac cagcaaggca aactcagcgg aaactgtttc tttcagctgg     120
aacaagttcg tgccgaagca accaaacatg atcctccaag agacgctat tgtgacctcc      180
tcgggaaagt acaactcaa taaggttgac gaaaacggca ccccaaaacc ctcgtctctt      240
ggtcgcgccc tctactccac ccccatccac atttgggaca agaaaccgg tagcgttgcc      300
agcttcgccg cttccttcaa cttcaccttc tatgccctg acacaaaaag gcttgcagat      360
gggcttgcct ctttctcgc accaattgac actaagccac aaacacatgc aggttatctt      420
ggtcttttca cgaaaacga gtctggtgat caagtcgtcg ctgttgagtt tgacactttc      480
cggaactctt gggatccacc aaatccacac atcggaatta acgtcaattc tatcagatcc      540
atcaaaacga cgtcttggga tttggccaac aataaagtag ccaaggttct cattacctat      600
gatgcctcca ccagcctctt ggttgcttct ttggtctacc cttcacagag aaccagcaat      660
atcctctccg atgtggtcga tttgaagact tctcttcccg agtgggtgag gatagggttc      720
tctgctgcca cggactcga catacctggg gaatcgcatg acgtgctttc ttggtctttt      780
gcttccaatt tgccacacgc tagcagtaac attgatcctt tggatcttac aagctttgtg     840
ttgcatgagg ccatctaa                                                   858
```

<210> SEQ ID NO 6
<211> LENGTH: 285
<212> TYPE: PRT
<213> ORGANISM: Glycine max

<400> SEQUENCE: 6

```
Met Ala Thr Ser Lys Leu Lys Thr Gln Asn Val Val Ser Leu Ser
1               5                   10                  15

Leu Thr Leu Thr Leu Val Leu Val Leu Thr Ser Lys Ala Asn Ser
            20                  25                  30

Ala Glu Thr Val Ser Phe Ser Trp Asn Lys Phe Val Pro Lys Gln Pro
        35                  40                  45

Asn Met Ile Leu Gln Gly Asp Ala Ile Val Thr Ser Ser Gly Lys Leu
50                      55                  60

Gln Leu Asn Lys Val Asp Glu Asn Gly Thr Pro Lys Pro Ser Ser Leu
65                  70                  75                  80

Gly Arg Ala Leu Tyr Ser Thr Pro Ile His Ile Trp Asp Lys Glu Thr
                85                  90                  95

Gly Ser Val Ala Ser Phe Ala Ala Ser Phe Asn Phe Thr Phe Tyr Ala
            100                 105                 110

Pro Asp Thr Lys Arg Leu Ala Asp Gly Leu Ala Phe Phe Leu Ala Pro
        115                 120                 125

Ile Asp Thr Lys Pro Gln Thr His Ala Gly Tyr Leu Gly Leu Phe Asn
130                 135                 140

Glu Asn Glu Ser Gly Asp Gln Val Val Ala Val Glu Phe Asp Thr Phe
145                 150                 155                 160

Arg Asn Ser Trp Asp Pro Pro Asn Pro His Ile Gly Ile Asn Val Asn
                165                 170                 175

Ser Ile Arg Ser Ile Lys Thr Thr Ser Trp Asp Leu Ala Asn Asn Lys
            180                 185                 190

Val Ala Lys Val Leu Ile Thr Tyr Asp Ala Ser Thr Ser Leu Leu Val
        195                 200                 205

Ala Ser Leu Val Tyr Pro Ser Gln Arg Thr Ser Asn Ile Leu Ser Asp
210                 215                 220

Val Val Asp Leu Lys Thr Ser Leu Pro Glu Trp Val Arg Ile Gly Phe
225                 230                 235                 240

Ser Ala Ala Thr Gly Leu Asp Ile Pro Gly Glu Ser His Asp Val Leu
                245                 250                 255

Ser Trp Ser Phe Ala Ser Asn Leu Pro His Ala Ser Asn Ile Asp
            260                 265                 270

Pro Leu Asp Leu Thr Ser Phe Val Leu His Glu Ala Ile
            275                 280                 285

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
ccagcaaaca acacaacaga gcagcaaag                                    29

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
ctccacgcat ttcctccaat ttcactctat atctg                             35
```

```
<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
ggaaggaggc agcttgtaat gccgtattt                                      29

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
acatgtttcc tcattgtatt tgtcttggcc tctt                                34

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
gggaaagagc ggatacattg caaagtgc                                       28

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
tggataccaa atttagctca gatggagggt tatt                                34

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
cttcgttggc ttgggcactt ctcaaatc                                       28

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
agaaacctca ctttgaaata ccggagggc                                      29

<210> SEQ ID NO 15
<211> LENGTH: 33
<212> TYPE: DNA
<213> ORGANISM: Artificial Sequence
<220> FEATURE:
<223> OTHER INFORMATION: Primer
```

```
<400> SEQUENCE: 15
gaggatggat ttaaaccagt cagcaccgta agt                                         33

<210> SEQ ID NO 16
<211> LENGTH: 32
<212> TYPE: DNA
<213> ORGANISM: Artificial Sequence
<220> FEATURE:
<223> OTHER INFORMATION: Primer

<400> SEQUENCE: 16
gttgctgctg ttcttgtttg ctctgcgtta ct                                          32

<210> SEQ ID NO 17
<211> LENGTH: 8
<212> TYPE: PRT
<213> ORGANISM: Artificial
<220> FEATURE:
<223> OTHER INFORMATION: Consensus peptide sequence
<220> FEATURE:
<221> NAME/KEY: MISC_FEATURE
<222> LOCATION: (2)..(5)
<223> OTHER INFORMATION: X = any amino acid

<400> SEQUENCE: 17

Gly Xaa Xaa Xaa Xaa Gly Lys Ser
1               5
```